(12) United States Patent
Kuhr et al.

(10) Patent No.: US 7,826,250 B2
(45) Date of Patent: Nov. 2, 2010

(54) OPEN CIRCUIT POTENTIAL AMPEROMETRY AND VOLTAMMETRY

(75) Inventors: Werner G. Kuhr, Oak Hills, CA (US);
David F. Bocian, Riverside, CA (US);
Jonathan S. Lindsey, Raleigh, NC (US);
Kristian A. Roth, Riverside, CA (US)

(73) Assignee: North Carolina State Univeristy, Raleigh, NC (US)

( * ) Notice: Subject to any disclaimer, the term of this patent is extended or adjusted under 35 U.S.C. 154(b) by 1479 days.

(21) Appl. No.: 11/102,089

(22) Filed: Apr. 7, 2005

(65) Prior Publication Data

US 2005/0185447 A1     Aug. 25, 2005

Related U.S. Application Data

(62) Division of application No. 10/098,996, filed on Mar. 14, 2002, now Pat. No. 6,921,475.

(60) Provisional application No. 60/278,555, filed on Mar. 23, 2001.

(51) Int. Cl.
*G11C 11/00* (2006.01)
(52) U.S. Cl. ........................ 365/151; 365/174
(58) Field of Classification Search ............ 365/151, 365/174
See application file for complete search history.

(56) References Cited

U.S. PATENT DOCUMENTS

| | | | |
|---|---|---|---|
| 3,637,581 A | 1/1972 | Horiguchi et al. | |
| 3,833,894 A | 9/1974 | Aviram et al. | |
| 4,618,509 A | 10/1986 | Bulkowski | |
| 4,663,270 A | 5/1987 | Potember et al. | |
| 4,670,860 A | 6/1987 | Wilson | |
| 4,728,724 A | 3/1988 | Jones et al. | |
| 4,781,443 A | 11/1988 | Giles | |
| 5,010,451 A | 4/1991 | Ueyama et al. | |

(Continued)

FOREIGN PATENT DOCUMENTS

EP     0 272935 A3     6/1988

(Continued)

OTHER PUBLICATIONS

Han et al. (2000) "Analysis of Open-Circuit Potential Transient and Laser Beam Deflection Transient Simultaneously Measured from Pd Foil Electrode Pre-Charged with Hydrogen" Electrochimica Acta 45: 2781-2790.

(Continued)

*Primary Examiner*—Vu A Le
*Assistant Examiner*—Han Yang
(74) *Attorney, Agent, or Firm*—Weaver Austin Villeneuve & Sampson LLP

(57) ABSTRACT

This invention provides approaches to improve the signal to noise ratio (S/N) in electrochemical measurements (e.g., amperometry, voltammetry, etc.). In particular, a method is described wherein the faradaic current is temporally dissociated from the charging current associated with reading the charge of a redox-active species (e.g., a self-assembled monolayer (SAM)). This method, designated herein as open circuit potential amperometry (OCPA), quantitatively reads the charge of the redox species bound to (electrically coupled to) an electrode surface, while discriminating against both charging current(s) and amperometric signal(s) that arise, e.g., from diffusion-based species in solution.

8 Claims, 16 Drawing Sheets

U.S. PATENT DOCUMENTS

| | | | |
|---|---|---|---|
| 5,016,063 | A | 5/1991 | Beratan et al. |
| 5,035,835 | A | 7/1991 | Asakawa et al. |
| 5,063,417 | A | 11/1991 | Hopfield |
| 5,075,738 | A | 12/1991 | Matsuda et al. |
| 5,091,502 | A | 2/1992 | Narang et al. |
| 5,135,537 | A | 8/1992 | Eida et al. |
| 5,222,060 | A | 6/1993 | Kuroda et al. |
| 5,252,698 | A | 10/1993 | Bhardwaj et al. |
| 5,264,876 | A | 11/1993 | Kawade et al. |
| 5,280,183 | A | 1/1994 | Batzel et al. |
| 5,312,762 | A | 5/1994 | Guiseppi-elie |
| 5,312,896 | A | 5/1994 | Bhardwaj et al. |
| 5,432,379 | A | 7/1995 | Eguchi et al. |
| 5,434,842 | A | 7/1995 | Weiss et al. |
| 5,463,014 | A | 10/1995 | Epstein et al. |
| 5,466,349 | A | 11/1995 | Tench et al. |
| 5,475,075 | A | 12/1995 | Brant et al. |
| 5,506,420 | A | 4/1996 | Kossovsky et al. |
| 5,525,811 | A | 6/1996 | Sakurai et al. |
| 5,539,100 | A | 7/1996 | Wasielewski et al. |
| 5,547,774 | A | 8/1996 | Gimzewski et al. |
| 5,707,845 | A | 1/1998 | Ueyama et al. |
| 5,744,598 | A | 4/1998 | Skalkos et al. |
| 5,804,850 | A | 9/1998 | Evans, Jr. et al. |
| 5,814,420 | A | 9/1998 | Chu |
| 5,840,443 | A | 11/1998 | Gregg et al. |
| 5,844,055 | A | 12/1998 | Brandt et al. |
| 5,858,666 | A | 1/1999 | Weiss |
| 6,013,170 | A | 1/2000 | Meade |
| 6,031,756 | A | 2/2000 | Gimzewski et al. |
| 6,060,327 | A | 5/2000 | Keen |
| 6,128,214 | A | 10/2000 | Kuekes et al. |
| 6,143,164 | A | 11/2000 | Heller et al. |
| 6,208,553 | B1 | 3/2001 | Gryko et al. |
| 6,212,093 | B1 | 4/2001 | Lindsey |
| 6,251,260 | B1 | 6/2001 | Heller et al. |
| 6,272,038 | B1 | 8/2001 | Clausen et al. |
| 6,324,091 | B1 | 11/2001 | Gryko et al. |
| 6,381,169 | B1 | 4/2002 | Bocian et al. |
| 6,451,942 | B1 * | 9/2002 | Li et al. ............ 526/258 |
| 7,695,756 | B2 * | 4/2010 | Gallo et al. ........... 427/58 |
| 2008/0219041 | A1 * | 9/2008 | Kuhr et al. .......... 365/151 |

FOREIGN PATENT DOCUMENTS

| | | |
|---|---|---|
| EP | 0 307210 A2 | 3/1989 |
| EP | 0 307211 A2 | 3/1989 |
| EP | 0 363147 A2 | 4/1990 |
| FR | 2700393 | 1/1993 |
| WO | WO 99/24527 A1 | 5/1999 |
| WO | WO 01/03126 A2 | 1/2001 |
| WO | WO/02/077633 | 10/2002 |

OTHER PUBLICATIONS

Roth et al. (2002) "Characterization of Charge Storage in Redox-Active Self-Assembled Monolayers", Langmuir 18: 4030-4040.

"Ferrocene—Molecule of the Month" Jun. 1996, University of Oxford Web Page, http://www.ncl.ox.ac.uk/mom/ferrocene/ferrocene2.html.

"Ferrocene—Synthesis", Jun. 1996, University of Oxford Web Page, http://www.ncl.ox.ac.uk/mom/ferrocene/synthesis.html.

Ball et al. (2000) "Electrochemistry in Nanovials Fabricated by Combining Screen Printing and Laser Micromachining" Anal. Chem. 72: 497-501.

Bansal et al. (1998) "Electrochemical Properties of (111)-Oriented n-Si Surfaces Derivatized and Covalently-Attached Alkyl Chains" J. Phys. Chem. 102:7:1067-1070.

Bateman et al. (1998) Alkylation of Porous Silicon by Direct Reaction with Alkenes and Alkynes Angew. Chem. Int. Ed. 37:19:2683-2685.

Boukherroub et al. (1999) "Controleed Functionalization and Multistep Chemical Manipulation of Covalently Modified Si(111) Surfaces" J. Am. Chem. Soc. 21: 11513-11515.

Bratten et al. (1997) Micromachining Sensors for Electrochemical Measurement in Subnanoliter Volumes Anal. Chem. 69: 253-259.

Buchler and Ng (2000) in *The Porphyrin Handbook*, vol. 3, pp. 245-294, Eds. K. M. Kadish, K. M. Smith, R. Guilard, Academic Press, San Diego, CA.

Buriak et al. (1998) "Lewis Acid Mediated Functionalization of Porous Silicon with Substituted Alkeses and Alkynes" J. Am. Chem. Soc. 120: 1339-1340.

Chabach et al. (1996) "Mixed-Metal Triple-Decker Sandwich Complexes with the Porphyrin/Phthalocynine/Porphyrin Ligand System" *Angew. Chem. Int. Ed. Engl.*, 35: 898.

Clausen et al. (2000) Investigation of Tightly Coupled Porphyrin Arrays Comprised of Identical Monomers for Multibit Information Storage, J. Org. Chem. 65: 7371-7378.

Cleland et al. (1995) "Direct Functionalization of Silicon via the Self-Assembly of Alcohols" J. Chem. Soc. Faraday Trans. 91(21) 4001-4003.

Clark et al. (1997) "Electrochemical Analysis in Picoliter Microvials" Anal. Chem. 69: 259-263.

Clark et al. (1998) "Characterization of Electrochemical Responses in Picoliter Volumes" Anal. Chem. 70: 1119-1125.

Collier et al. (1999) "Electronically Configurable Molecular-Based Logic Gates" Science 265: 391-394.

Cotton et al (1976) Basic Inorganic Chemistry, pp. 125, 497, 518.

Coulter et al. (2000) "Reactions of Substituted Aromatic Hydrocarbons with the Si(001)Surface" J. Vac. Sci. Technol. A 18(4) 1965-1970.

Duchowski et al. (1990) Spectroscopic Characerization of Triple Decker Lanthanide Porphyrin Sandwich Complexes. Effects of Strong $\pi$ $\pi$ Interactions in Extended Assemblies J Am. Chem. Soc. 112: 8807-8811.

Gavin et al. (1996) "Continuous Separations with Microfabricated Electrophoresis-Electrochemical Array Detection" J. Am Chem. Soc. 118: 8932-8936.

Gorman (1997) "Encapsulated Electroactive Molecules" Adv. Mater. 9(14) 1117-1119.

Gorman (1999) "Molecular Structure-Property Relationships for Electron-Transfer Rate Attenuation in Redox-Active Core Dendrimers" J. Am. Chem. Soc. 121: 9958-9966.

Gross (2001) "Investigation of Rational Synthesis of Heteroleptic Porphyrinic Lanthanide (Europium, Cerium) Triple-Decker Sandwich Complexes" Inorg. Chem. 40: 4762-4774.

Gryko (2000) "Synthesis of Porphyrin-Linker-Thiol Molecules with Diverse Linkers for Studies of Molecular-Based Information Storage" J. Org. Chem. 65: 7345-7355.

Gryko (2000) "Synthesis of Thiol-Derivatized Ferrocene-Porphrins for Studies of Multibit Information Storage" J. Org. Chem. 65: 7356-7362.

Gryko (2001) "Studies Related to the Design and Synthesis of a Molecular Octal Counter" J. Mater. Chem. 11: 1162-1180.

Hyde (1985) "Ellipsometric Measurements of the Pt-Aqueous Electrolyte Interface, in the Absence and in the Presence of Specific Anionic Adsorption" J. Electroanal. Chem. 186: 267-286.

Jiang et al. (1998) "Heteroleptic Triple-Decker (Phthalocyaninato)-Porphyrinato) Europium (III) Complexes: Synthesis and Electrochemical Study" Inorganica Chimica Acta 268: 49-53.

Kovach et al. (1985) "Faradaic Electrochemistry at Microcylinder, Band, and Tubular Band Electrodes" 185: 285-295.

Li et al. (2000) "Synthesis of Thiol-Derivatized Europium Porphyrinic Triple-Decker Sandwich Complexes for Multibit Molecular Information Storage" J. Org. Chem. 65: 7379-7390.

Nagale et al. (1998) "Individually Addressable, Submicrometer Band Electrode Arrays. 1. Fabrication from Multilayered Materials" Anal. Chem. 70: 2902-2907.

Roth (2000) "Molecular Approach Toward Information Storage Based on the Redox Properties of Porphyrins in Self-Assembled Monolayers" J. Vac. Sci. Technol. B. 18(5) 2359-2364.

Ruben et al. (2000) "Multilevel Molecular Electronic Species: Electrochemical Reduction of a [2X2] Co4 Grid Type Complex by 11 Electrons in 10 Reversible Steps" Angew. Chem. Int. Ed. 39(22) 4139-4142.

Sommerauer et al. (1996) "Separation of 1(3), 9(10), 16(17), 23(24)-Tetrasubstituted Phthalycyanines with Newly Developed HPLC Phases" J. Am Chem. Soc. 118: 10085-10093.

Wong et al. (1974) "Lanthanide Porphyrin Complexes, A Potential New Class of Nuclear Magnetic Resonance Dipolar Probe" J. Am. Chem. Soc. 96(22) 7149-7150.

Zhu et al. (1999) "Chemical Vapor Deposition of Organic Momolayers on Si(100) via Si—N Linkages" Langmuir 15: 8147-8154.

International Search Report dated Jul. 9, 2002 issued in WO/2002/077633 (PCT/US2002/07909).

International Preliminary Examination Report dated Oct. 27, 2003 issued in WO/2002/077633 (PCT/US2002/07909).

US Notice of Allowance dated Feb. 9, 2005 issued in U.S. Appl. No. 10/098,996.

Rosamillia et al., "Electrochemical examination of the copper oxidation state in the fluorine doped $Nd_2CuO_4$" J. Electroanal. Chem. (1990); 291:163-170.

* cited by examiner

OPEN CIRCUIT POTENTIAL AMPEROMETRY AND VOLTAMMETRY

CROSS-REFERENCE TO RELATED APPLICATIONS

This application is a Divisional of U.S. Ser. No. 10/098,996, filed on Mar. 14, 2002 which claims benefit of and priority to U.S. Ser. No. 60/278,555, filed on Mar. 23, 2001, both of which are incorporated herein by reference in their entirety for all purposes.

STATEMENT AS TO RIGHTS TO INVENTIONS MADE UNDER FEDERALLY SPONSORED RESEARCH AND DEVELOPMENT

This work was supported by the DARPA Moletronics Program, administered by the Office of Naval Research (ONR) grant number N00014-99-0357. The government of the United States of America may have certain rights in this invention.

FIELD OF THE INVENTION

This invention relates the field of electrochemistry. In particular, this invention provides improved amperometric and voltammetric methods.

BACKGROUND OF THE INVENTION

There is an increasing interest in the development of arrays of surface-immobilized molecules for use as sensors, where molecular selectivity is achieved through a binding reaction with a sensor element often comprising a biological macromolecule (e.g., nucleic acid, protein, etc.). Thus, for example, strategies for the detection/quantification of nucleic acids can utilize arrays of DNA probes ready for hybridization. The nucleic acid to be analyzed is isolated and labeled with a fluorescent reporter group (Fidanza and McGall (1999) *Nucleosides & Nucleotides*, 18: 1293-1295; Lipshutz et al. (1999) *Nature Genetics Chipping Forecast*, 21: 20-24) and then hybridized to (incubated with) the array. The hybridization data are collected, e.g., as fluorescence emission from the label incorporated into the nucleic acid(s) hybridized to the probe array. Because the sequence and position of each probe on the array is known, the identity of the bound target nucleic acid is readily determined.

Similar approaches have been proposed that use microfabricated fiber optics to create high-density arrays of randomly ordered self-assembled bead-based sensors (Michael et al. (1998) *Anal. Chem.* 70: 1242-1248). Alternatively, semiconductor devices have been developed where small nucleic acids, or other capture probes, are electronically placed at, or "addressed" to, specific sites on a microchip. A sample is then analyzed for the presence of target molecules by determining which of the capture probes on the array bind to their cognate analyte in the sample (Edman et al. (1998) *Nucl. Acids Res.*, 25: 4907-4914; Cheng et al. (1998) *Nature Biotechnology*, 16: 541-546).

SUMMARY OF THE INVENTION

This invention provides methods for detecting or quantifying the presence of a target moiety attached to, or associated with a sensor and/or to determine the redox-state of a particular target moiety. In particular, the methods of this invention involve the electrochemical detection of the redox state of one or more target moieties. Thus, where the methods are used in a sensor, a change in redox state of a sensor element (e.g., nucleic acid, antibody, lectin, etc.) caused by the binding of a target analyte is detected. In other applications, e.g., molecular memories, the redox state of the storage molecules, or other analytes is determined using electrochemical methods.

In certain embodiments, this invention provides approaches to improve the signal to noise ratio (S/N) in electrochemical measurements (e.g., amperometry, voltammetry, etc.). In particular, a method is described wherein the faradaic current is temporally dissociated from the charging current associated with reading the charge of a redox-active species (e.g., a self-assembled monolayer (SAM)). This method, designated herein as open circuit potential amperometry (OCPA), quantitatively reads the charge of the redox species bound to (electrically coupled to) an electrode surface, while discriminating against both charging current(s) and amperometric signal(s) that arise, e.g., from diffusion-based species in solution.

Voltammetric data can also be obtained using this methodology. In this method, designated open circuit potential voltammetry (OPCV), a series of OCPA steps is preformed in which the potential is successively incremented (similar to pulse voltammetric methods). The efficacies of OCPA and OPCV are demonstrated herein in Example 1 using two types of thiol-derivatized, redox-active molecules attached to Au: (1) an alkyl-ferrocene and (2) a Zn tetraarylporphyrin. The Examples provided herein show that OPCA and OPCV permit the accurate measurement of the charge associated exclusively with the electrode-coupled redox species with very high signal quality in a very short time period.

Thus, in one embodiment this invention provides methods of determining the oxidation state of a compound. The methods preferably involve disconnecting an electrode from an electrochemical cell comprising the compound being measured (e.g., a redox-active compound) to allow the cell to reach an open circuit potential (OCP), connecting said electrochemical cell to an externally applied potential equivalent to the open circuit potential; and detecting a resulting current if such current exists where the magnitude of the current is a measure of the oxidation state of said compound. In particularly preferred embodiments, the compound is oxidized and said open circuit potential is a reducing potential, while certain other embodiments the compound is reduced and said open circuit potential is an oxidizing potential. The disconnecting is typically for a period ranging from about 0.001 ms to about 60 seconds, preferably from about 0.01 ms to about 20 s, more preferably from about 0.01 ms to about 1 s, and most preferably from about 0.001 ms to about 0.1 s. In certain embodiments, the electrochemical cell a member of an array of electrochemical cells (e.g., an array comprising at least 10, preferably at least 100, more preferably at least 1000, and most preferably at least 10,000 or at least 1,000,000 electrochemical cells. In certain embodiments the cells comprise a molecular memory or a biosensor.

The disconnecting and connecting can comprise disconnecting and connecting the same electrode. In certain embodiments the disconnecting and connecting comprise making or breaking an electrical connection. In certain embodiments the disconnecting and connecting comprise varying a resistance between an electrode and the cell. In preferred embodiments, the open circuit potential (OCP) varies from about −5 V to about 5V, more preferably from about −2 V to about +2 V, still more preferably from about −1 V to about +1 V, and most preferably from about −0.5 V to about +0.5 V.

In certain preferred embodiments, the redox-active compound measured in the potentiostat of this invention has a multiplicity of different and distinguishable non-zero oxidation states (e.g., at least 2, preferably at least 4, more preferably at least 8, and most preferably at least 16, 32, or 64 different and distinguishable oxidation states). Particularly preferred redox-active compounds include, but are not limited to, porphyrinic macrocycles (e.g., as described in WO 01/03126).

In certain embodiments the potential is applied to the electrochemical cell through a voltage follower. In various embodiments, the potential is applied through a counter electrode while a working electrode is held at ground. Signal detection can be by any convenient method, e.g., amplifying the current with a high bandwidth current amplifier.

In another embodiment, this invention provides a method of determining the oxidation state of a compound by applying a series of incrementally increasing voltage pulses to the compound in an electrochemical cell, disconnecting an electrode from the electrochemical cell, after each pulse, to allow the cell to reach an open circuit potential (OCP); connecting the electrochemical cell to an externally applied potential equivalent to said open circuit potential; and detecting a resulting current if said current exists wherein the magnitude of the current is a measure of the oxidation state of said compound. In certain preferred embodiments, the compound is oxidized and the open circuit potential is a reducing potential, while in other embodiments, the compound is reduced and said open circuit potential is an oxidizing potential.

The disconnect time is typically for a period ranging from about 0.001 ms to about 60 seconds, preferably from about 0.01 ms to about 20 s, more preferably from about 0.01 ms to about 1 s, and most preferably from about 0.001 ms to about 0.1 s. In certain embodiments, the electrochemical cell a member of an array of electrochemical cells (e.g., an array comprising at least 10, preferably at least 100, more preferably at least 1000, and most preferably at least 10,000 or at least 1,000,000 electrochemical cells.

The disconnecting and connecting can comprise disconnecting and connecting the same electrode. In certain embodiments the disconnecting and connecting comprise making or breaking an electrical connection. In certain embodiments the disconnecting and connecting comprise varying a resistance between an electrode and the cell. In preferred embodiments, the open circuit potential (OCP) varies from about −5 V to about 5 V, more preferably from about −2 V to about +2 V, still more preferably from about −1 V to about +1 V, and most preferably from about −0.5 V to about +0.5 V.

In certain embodiments the potential is applied to the electrochemical cell through a voltage follower. In various embodiments, the potential is applied through a counter electrode while a working electrode is held at ground. Signal detection can be by any convenient method, e.g., amplifying the current with a high bandwidth current amplifier.

In certain preferred embodiments, the redox-active compound measured in the potentiostat of this invention has a multiplicity of different and distinguishable non-zero oxidation states (e.g., at least 2, preferably at least 4, more preferably at least 8, and most preferably at least 16, 32, or 64 different and distinguishable oxidation states). Particularly preferred redox-active compounds include, but are not limited to, porphyrinic macrocycles (e.g., as described in WO 01/03126).

In certain embodiments the potential is applied to the electrochemical cell through a voltage follower. In various embodiments, the potential is applied through a counter electrode while a working electrode is held at ground. Signal detection can be by any convenient method, e.g., amplifying the current with a high bandwidth current amplifier.

In still another embodiment, this invention provides a device for the detection of an oxidation state of a compound. The device typically comprises a first electrode and a second electrode disposed to contact the compound and thereby form an electrochemical cell; a voltage source connected to said first electrode; a switch that allows the compound to be isolated from the voltage source and the electrochemical cell to reach an open circuit potential; and a current measuring device for measuring current produced by the electrochemical cell. In certain embodiments, the device comprises two or more electrochemical cells, i.e., the electrochemical cell a member of an array of electrochemical cells (e.g., an array comprising at least 10, preferably at least 100, more preferably at least 1000, and most preferably at least 10,000 or at least 1,000,000 electrochemical cells. In certain embodiments the voltage source comprises a voltage follower. In certain embodiments the current measuring device comprises a broadband current amplifier.

In various embodiments, the first electrode and the second electrode are disposed in a channel (e.g., a capillary tube, a channel on a chip, an open-topped channel, etc.) through which a fluid comprising said compound can pass. In certain embodiments the electrodes are disposed in a well (e.g., in a multi-well plate). The electrodes can be disposed on a biosensor. The electrodes, in certain embodiments, are components of a molecular memory.

In still another embodiment, this invention provides a molecular memory device comprising a first electrode and a second electrode disposed to contact a redox-active compound comprising a porphyrinic macrocycle (e.g., a porphyrin) and thereby form an electrochemical storage cell wherein the first and second electrodes are fixed electrodes; a voltage source connected to the first electrode; a switch (switching device) that allows the redox-active compound to be isolated from the voltage source and the storage cell to reach an open circuit potential; and a current measuring device for measuring current produced by the electrochemical cell. In certain embodiments, the device comprises two or more electrochemical cells, i.e., the electrochemical cell a member of an array of electrochemical cells (e.g., an array comprising at least 10, preferably at least 100, more preferably at least 1000, and most preferably at least 10,000 or at least 1,000,000 electrochemical cells. In certain embodiments the voltage source comprises a voltage follower. In certain embodiments the current measuring device comprises a broadband current amplifier.

DEFINITIONS

The term "oxidation" refers to the loss of one or more electrons in an element, compound, or chemical substituent/subunit. In an oxidation reaction, electrons are typically lost by atoms of the molecule(s) involved in the reaction. The charge on these atoms then becomes more positive. The electrons are lost from the species undergoing oxidation and so electrons appear as products in an oxidation reaction. An oxidation is taking place in the reaction $Fe^{2+}(aq) \rightarrow Fe^{3+}(aq) + e^-$ because electrons are lost from the species being oxidized, $Fe^{2+}(aq)$, despite the apparent production of electrons as "free" entities in oxidation reactions. Conversely the term reduction refers to the gain of one or more electrons by an element, compound, or chemical substituent/subunit.

An "oxidation state" refers to the electrically neutral state or to the state produced by the gain or loss of electrons to an element, compound, or chemical substituent/subunit. In a preferred embodiment, the term "oxidation state" refers to states including the neutral state and any state other than a neutral state caused by the gain or loss of electrons (reduction or oxidation).

The term "multiple oxidation states" means more than one oxidation state. In preferred embodiments, the oxidation states may reflect the gain of electrons (reduction) or the loss of electrons (oxidation).

The terms "different and distinguishable" when referring to two or more oxidation states means that the net charge on the entity (atom, molecule, aggregate, subunit, etc.) can exist in two different states. The states are said to be "distinguishable" when the difference between the states is greater than that provided by thermal energy at room temperature (e.g., 0° C. to about 40° C.).

The term "electrode" refers to any medium capable of transporting charge (e.g., electrons) to and/or from a storage molecule. Preferred electrodes are metals or conductive organic molecules. The electrodes can be manufactured to virtually any 2-dimensional or 3-dimensional shape (e.g., discrete lines, pads, planes, spheres, cylinders, etc.).

The term "fixed electrode" is intended to reflect the fact that the electrode is essentially stable and unmovable with respect to the storage medium (redox active material). That is, the electrode and storage medium are arranged in an essentially fixed geometric relationship with each other. It is of course recognized that the relationship alters somewhat due to expansion and contraction of the medium with thermal changes or due to changes in conformation of the molecules comprising the electrode and/or the storage medium. Nevertheless, the overall spatial arrangement remains essentially invariant. In a preferred embodiment this term is intended to exclude systems in which the electrode is a movable "probe" (e.g., a writing or recording "head", an atomic force microscope (AFM) tip, a scanning tunneling microscope (STM) tip, etc.).

The term "electrically coupled" when used with reference to a storage molecule and/or storage medium (redox active material) and electrode refers to an association between that storage medium or molecule and the electrode such that electrons move from the storage medium/molecule to the electrode or from the electrode to the storage medium/molecule and thereby alter the oxidation state of the storage medium/molecule. Electrical coupling can include direct covalent linkage between the storage medium/molecule and the electrode, indirect covalent coupling (e.g., via a linker), direct or indirect ionic bonding between the storage medium/molecule and the electrode, or other bonding (e.g., hydrophobic bonding). In addition, no actual bonding may be required and the storage medium/molecule may simply be contacted with the electrode surface. There also need not necessarily be any contact between the electrode and the storage medium/molecule where the electrode is sufficiently close to the storage medium/molecule to permit electron tunneling between the medium/molecule and the electrode.

A "redox-active" compound or molecule refers to a compound or molecule capable of being oxidized or reduced.

The term "redox-active unit" or "redox-active subunit" refers to a molecule or component of a molecule that is capable of being oxidized or reduced by the application of a suitable voltage.

The term "subunit", as used herein, refers to a redox-active component of a molecule.

The terms "storage molecule" or "memory molecule" refer to a molecule having one or more oxidation states that can be used for the storage of information (e.g., a molecule comprising one or more redox-active subunits). Preferred storage molecules have two or more different and distinguishable non-neutral oxidation states.

The term "storage medium" refers to a composition comprising two or more storage molecules. The storage medium can contain only one species of storage molecule or it can contain two or more different species of storage molecule. In preferred embodiments, the term "storage medium" refers to a collection of storage molecules. Preferred storage media comprise a multiplicity (at least 2) of different and distinguishable (preferably non-neutral) oxidation states. The multiplicity of different and distinguishable oxidation states can be produced by the combination of different species of storage molecules, each species contributing to said multiplicity of different oxidation states and each species having a single non-neutral oxidation state. Alternatively or in addition, the storage medium can comprise one or more species of storage molecule having a multiplicity of non-neutral oxidation states. The storage medium can contain predominantly one species of storage molecule or it can contain a number of different storage molecules. The storage media can also include molecules other than storage molecules (e.g., to provide chemical stability, suitable mechanical properties, to prevent charge leakage, etc.).

The term "electrochemical cell" consists minimally of a reference electrode, a working electrode, a redox-active medium (e.g., a storage medium), and, if necessary, some means (e.g., a dielectric) for providing electrical conductivity between the electrodes and/or between the electrodes and the medium. In some embodiments, the dielectric is a component of the storage medium.

The terms "memory element", "memory cell", or "storage cell" refer to an electrochemical cell that can be used for the storage of information. Preferred "storage cells" are discrete regions of storage medium addressed by at least one and preferably by two electrodes (e.g., a working electrode and a reference electrode). The storage cells can be individually addressed (e.g., a unique electrode is associated with each memory element) or, particularly where the oxidation states of different memory elements are distinguishable, multiple memory elements can be addressed by a single electrode. The memory element can optionally include a dielectric (e.g., a dielectric impregnated with ions and counterions).

The term "storage location" refers to a discrete domain or area in which a storage medium is disposed. When addressed with one or more electrodes, the storage location may form a storage cell. However if two storage locations contain the same storage media so that they have essentially the same oxidation states, and both storage locations are commonly addressed, they may form one functional storage cell.

The terms "read" or "interrogate" refer to the determination of the oxidation state(s) of one or more molecules (e.g., molecules comprising a storage medium).

The term "refresh" when used in reference to a storage molecule or to a storage medium refers to the application of a voltage to the storage molecule or storage medium to re-set the oxidation state of that storage molecule or storage medium to a predetermined state (e.g., an oxidation state the storage molecule or storage medium was in immediately prior to a read).

The term "$E_{1/2}$" refers to the practical definition of the formal potential ($E°$) of a redox process as defined by $E=E°+(RT/nF)\ln(D_{ox}/D_{red})$ where R is the gas constant, T is temperature in K (Kelvin), n is the number of electrons involved in the process, F is the Faraday constant (96,485 Coulomb/mole), $D_{ox}$ is the diffusion coefficient of the oxidized species and $D_{red}$ is the diffusion coefficient of the reduced species.

A "voltage source" is any source (e.g., molecule, device, circuit, etc.) capable of applying a voltage to a target (e.g., an electrode).

A "voltammetric device" is a device capable of measuring the current produced in an electrochemical cell as a result of the application of a voltage or change in voltage.

An "amperometric device" is a device capable of measuring the current produced in an electrochemical cell as a result of the application of a specific potential ("voltage").

A "potentiometric device" is a device capable of measuring potential across an interface that results from a difference in the equilibrium concentrations of redox molecules in an electrochemical cell.

A "coulometric device" is a device capable of the net charge produced during the application of a potential field ("voltage") to an electrochemical cell.

A "sinusoidal voltammeter" is a voltammetric device capable of determining the frequency domain properties of an electrochemical cell.

The term "porphyrinic macrocycle" refers to a porphyrin or porphyrin derivative. Such derivatives include porphyrins with extra rings ortho-fused, or ortho-perifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral (meso-, β-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g., phthalocyanines, sub-phthalocyanines, and porphyrin isomers). Preferred porphyrinic macrocycles comprise at least one 5-membered ring. A number of porphyrinic macrocycles are described in WO 01/03126.

The term "porphyrin" refers to a cyclic structure typically composed of four pyrrole rings together with four nitrogen atoms and two replaceable hydrogens for which various metal atoms can readily be substituted. A typical porphyrin is hemin.

The term "multiporphyrin array" refers to a discrete number of two or more covalently-linked porphyrinic macrocycles. The multiporphyrin arrays can be linear, cyclic, or branched.

A "linker" is a molecule used to couple two different molecules, two subunits of a molecule, or a molecule to a substrate.

A "substrate" is a, preferably solid, material suitable for the attachment of one or more molecules. Substrates can be formed of materials including, but not limited to glass, plastic, silicon, germanium, minerals (e.g., quartz), semiconducting materials, ceramics, metals, etc.

The term "working electrode" typically used to refer to one or more electrodes that are used to set or read the state of a storage medium and/or storage molecule.

The term "reference electrode" is typically used to refer to one or more electrodes that provide a reference (e.g., a particular reference voltage) for measurements recorded from the working electrode. In certain embodiments, the reference electrode can be used to set a particular voltage. In preferred embodiments, the reference electrodes in a memory device of this invention are at the same potential although in some embodiments this need not be the case.

The term "fixed electrode" is intended to reflect the fact that the electrode is essentially stable and unmovable with respect to the storage medium. That is, the electrode and storage medium are arranged in an essentially fixed geometric relationship with each other. It is of course recognized that the relationship alters somewhat due to expansion and contraction of the medium with thermal changes or due to changes in conformation of the molecules comprising the electrode and/or the storage medium. Nevertheless, the overall spatial arrangement remains essentially invariant. In a preferred embodiment this term is intended to exclude systems in which the electrode is a movable "probe" (e.g., a writing or recording "head", an atomic force microscope (AFM) tip, a scanning tunneling microscope (STM) tip, etc.).

"Disconnecting an electrode" refers to an "increasing the impedance" of the circuit, e.g., by addition of a resistive element in series with a counter or working electrode.

"Connecting an electrode means" refers to decreasing the impedance of the circuit, e.g., by removing a resistive element in series with the counter or working electrode.

An "open circuit" condition is the state where a circuit contains a large current limiting, series impedance, preferably greater than $10 \times 10^6$ ohm (Mega ohm), more preferably greater than 100 Mohm, most preferably greater than $10^9$ ohm (1 Giga Ohm).

A "closed circuit" condition is the state where a circuit has low impedance to ground, preferably less than $10 \times 10^6$ ohm (Mega ohm), more preferably less than 100 kohm, most preferably less than 10 kohm (10,000 ohm).

A "switch" is a component in a circuit that changes state from high impedance ("open circuit") to low impedance ("closed circuit").

BRIEF DESCRIPTION OF THE DRAWINGS

FIG. 4A: The OCP is determined by incrementing the potential applied to the counter electrode, disconnecting (dashed dotted line) it for a time period ($\tau_1$=15 s), the circuit is reconnected (dotted line) and the resulting current FIG. 4B is monitored after reconnection and not during the subsequent potential step. At any potential other than OCP either a positive or negative current spike is observed as the electrochemical cell is charged to the applied potential. As $E_w$ approaches OCP, the current observed upon reconnection diminishes. The current nulls at the OCP. FIG. 4C: Empirical determination of the OCP of the $C_{12}Fc$ SAM. Each of the current transients shown represents the charging current observed upon reconnection of the electrochemical cell. Only charging (and not faradaic) current is observed because the potential steps are in a regime that is substantially less than the $E_{1/2}$ of the SAM. The OCP is the potential at which no current flows.

FIG. 5A: OCPA is performed by applying an oxidizing potential ($E_w$) at the working electrode via application of a negative potential at the counter electrode (during this process the working electrode is maintained at ground). A switch is then opened to disconnect the counter electrode (dotted line), thereby opening the electrochemical circuit for a specified time ($\tau_1$=15 s). After the potential of the electrochemical cell decays to the OCP, the switch is closed and the circuit is reconnected to an externally applied potential equal to the OCP of the reduced SAM ($E_R$: determined above), and the reductive current is monitored. The magnitude of the resulting current is directly proportional to the number of molecules that remain oxidized while the electrode is disconnected from the applied potential. In OCPA, only the disconnect time ($\tau$) is varied, while $E_W$ and $E_R$ are constant. FIG. 5B: OCPV is performed by first creating the oxidizing potential at the working electrode (EW1) and then incrementing this potential by a step ($\Delta E$). To obtain voltammetric data, the potential of the initial (oxidizing) pulse ($E_{W1}, E_{W2}, \ldots$) is varied, but the current is always measured at the OCP ($E_R$). Each successive oxidation step is incremented by the same potential step ($\Delta E = EW_2 - EW_1$). The current transients are only a result of reconnecting the counter electrode at ER and not from the potential step $\Delta E$. In OCPV, only EW is varied, while the disconnect time ($\tau_1$) and $E_R$ are kept constant.

FIG. 8A) and from 15 to 520 s for the ZnP SAM (electrode area=790 µm$^2$; FIG. 8B). The magnitude of the charge measured was found to decrease exponentially as a function of $\tau_1$, indicating a first order process for charge recombination. The charge measured at 25 µs in each trace was used to represent the total retained charge of the monolayer Q(t).

DETAILED DESCRIPTION

This invention provides approaches to improve the signal to noise ratio (S/N) in electrochemical measurements (e.g., amperometry, voltammetry, etc.). In general, the methods of this invention involve electrochemical measurements (e.g., voltammetry, amperometry, etc.) that temporally dissociate the faradaic current from the charging current associated with reading the oxidation state of a compound (e.g., reading the charge of a redox-active SAM). One method, designated herein as open circuit potential amperometry (OCPA), allows quantitative reading of the charge of a redox species, while discriminating against both charging currents and amperometric signals that arise from diffusion-based species in solution.

I. Open Circuit Potential Amperometry.

Open circuit potential amperometry (OCPA) is qualitatively similar to conventional chronoamperometry; however, these methods differ in that the measurement of the charge associated with the redox-active oxidized species being measured (e.g., a self assembling monolayer (SAM)) is temporally dissociated from the charging current. Temporal dissociation of these currents is accomplished by allowing the electrochemical cell in which the measurement is conducted to discharge to its open circuit potential (OCP) prior to the amperometric measurement. In certain preferred embodiments, each electrochemical cell has a characteristic open circuit potential (OCP) that can easily be ascertained, as described herein.

Figure 4A:
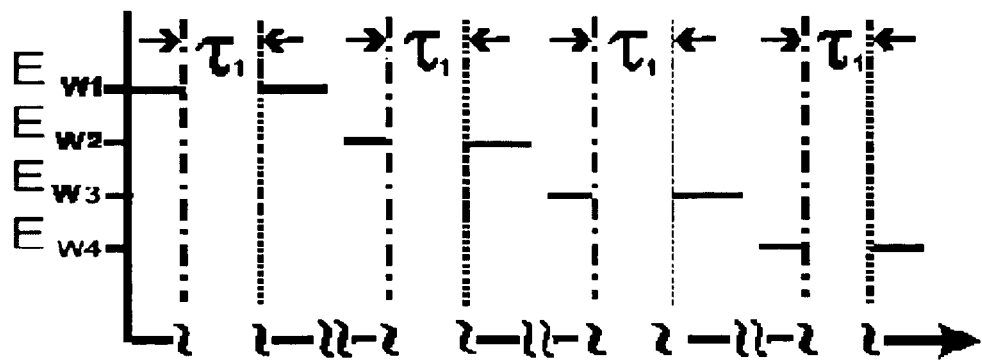
FIGS. 4A, 4B, and 4C illustrate the determination of the open circuit potential (OCP).
Figure 4B:
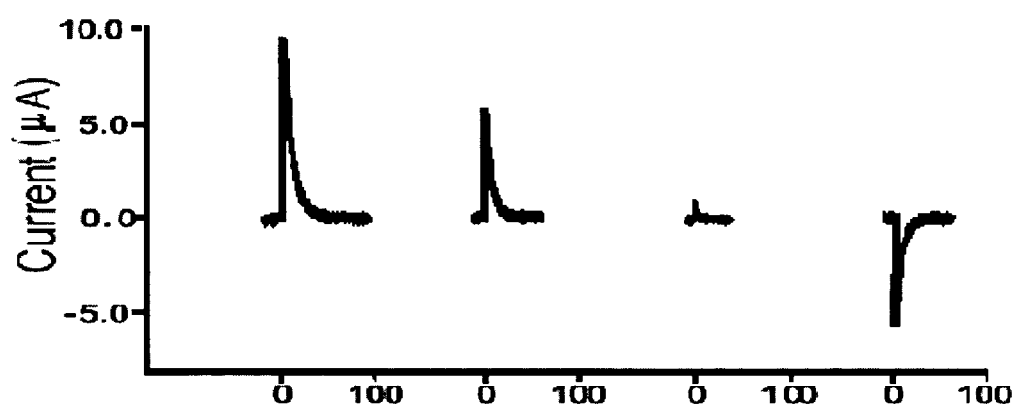
Figure 5A:
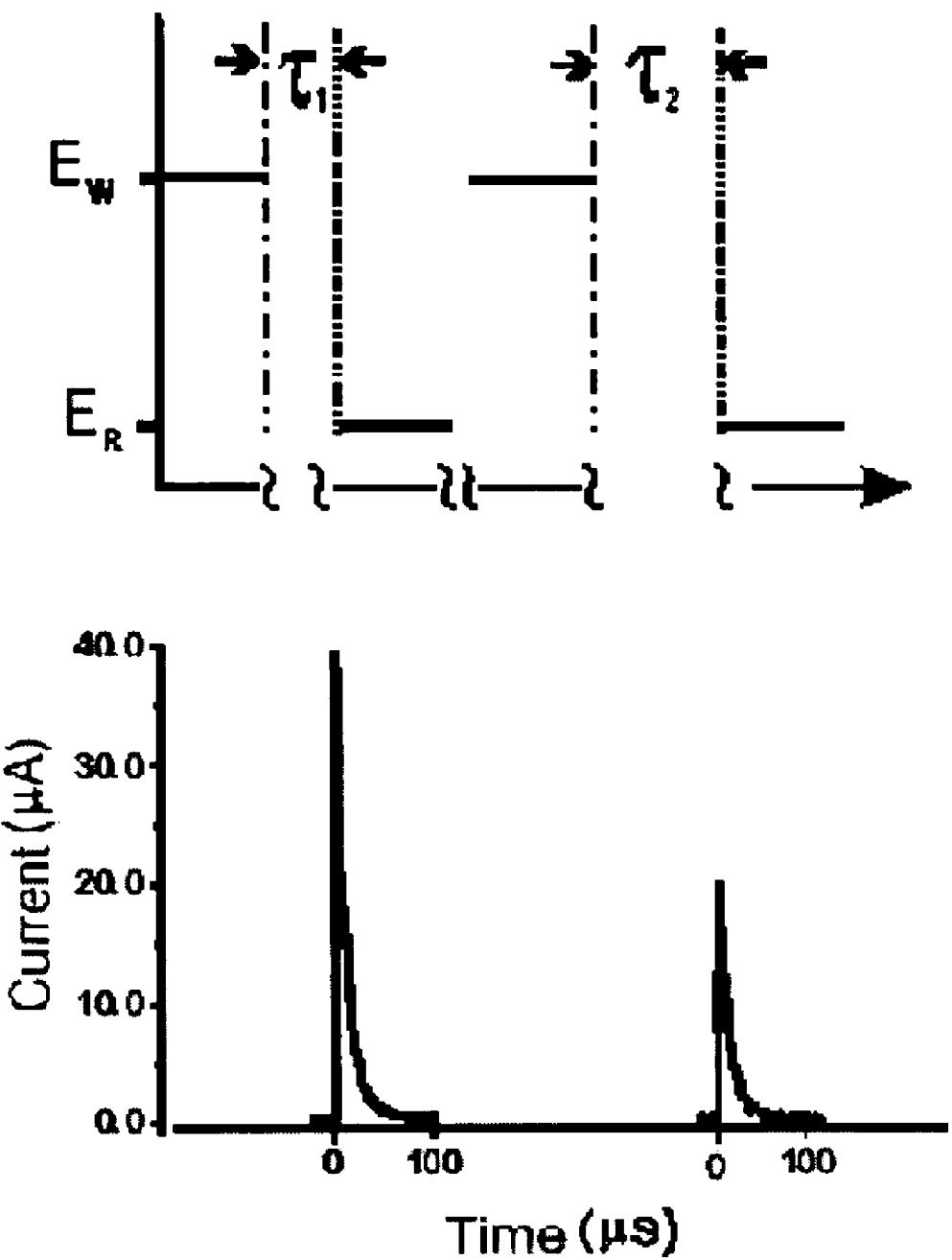
FIGS. 5A and 5B illustrate OCP amperometry and OCP voltammetry, respectively.

The "discharge" of the electrochemical cell to its OCP occurs due to the "imperfect" nature of the disconnected circuit. As will be shown below, even an "open" circuit, with very high impedance (>100 GΩ), passes enough current (picoamperes) to discharge an electrochemical cell containing a microelectrode to its OCP within seconds. Once the OCP has been reached, current is measured upon reconnection of the circuit to a potential equal to that of the OCP. This current arises primarily from the reduction of any molecules that are still oxidized in the species/sample being measured (FIG. 5A). In other words, after oxidation of the species/sample being measured (e.g., a storage molecule comprising a molecular memory), the circuit is left open for a sufficient time (disconnect time, $\tau_1$) to allow the charging current associated with the oxidation step to dissipate. Because the circuit is open, an electrode/electrolyte interface is produced in which the oxidized species/sample being measured is stable under open circuit conditions. Reconnection of the circuit with an applied potential equal to the OCP ($E_R$) reestablishes the electric field at the OCP without the need to inject any charging current into the cell (FIG. 4A). Upon reconnection of a low impedance path to the circuit, the oxidized species in the SAM are immediately reduced, producing a faradaic current (FIG. 4B).

While the foregoing discussion refers to determination of the oxidation state of an oxidized species the same approach can be used to measure the oxidation state of a reduced species.

II. Open Circuit Potential Voltammetry (OCPV).

Voltammetric data can also be obtained using this methodology. In the voltammetric method, designated open circuit potential voltammetry (OCPV), a series of OCPA steps is performed in which the potential is successively incremented (similar to pulse voltammetric methods).

Figure 5B:
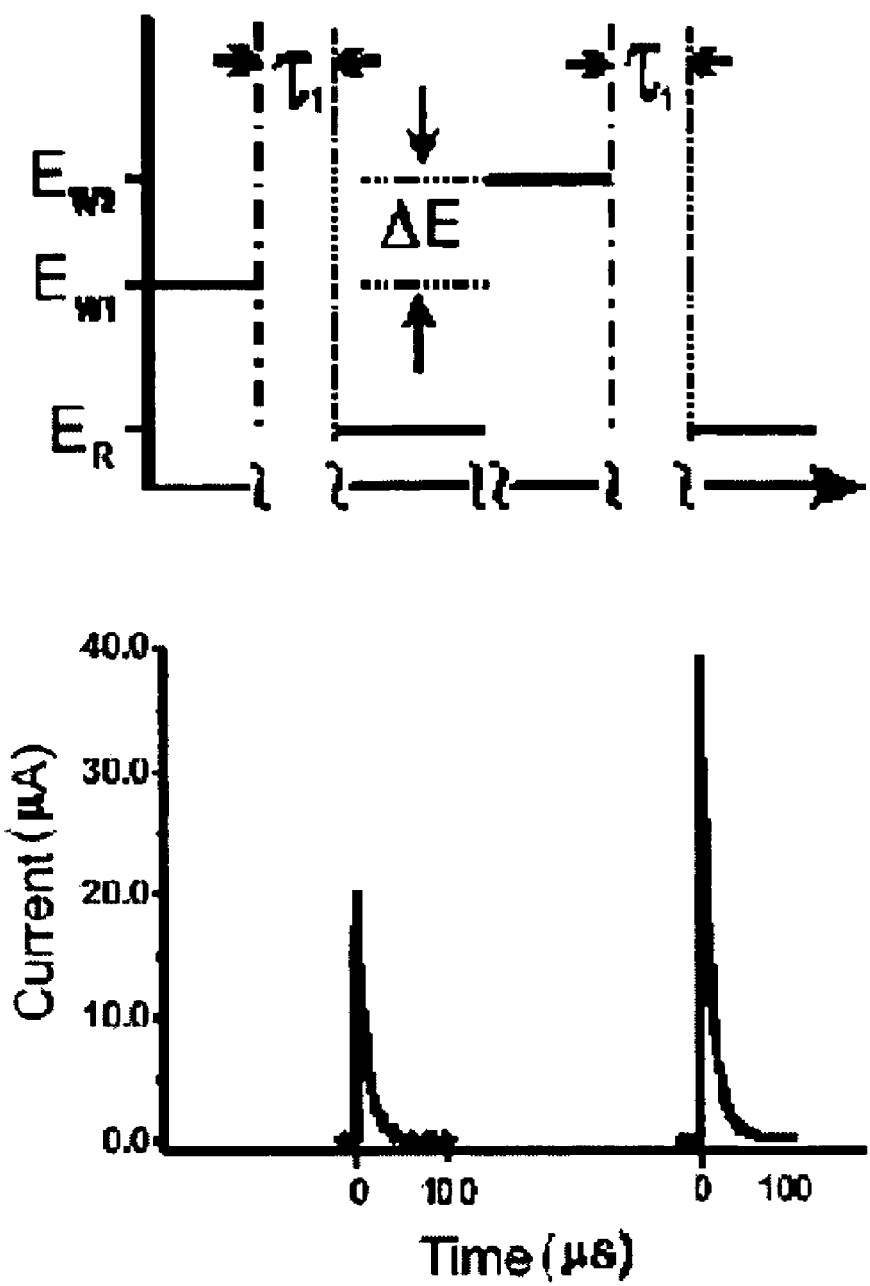

OCPV is schematically illustrated in FIG. 5B. The top panel in the figure illustrates the pulse sequence; the bottom panel shows the current response. OCPV is implemented by first applying an oxidation potential ($E_{W1}$) and then incrementing this potential by a step ($\Delta E$), similar to other pulse voltammetric methods. To obtain voltammetric data in this example, the potential of the oxidizing pulse ($E_{w1}$, $E_{w2}$, etc.) is varied, but the current is measured on the reductive step at the OCP ($E_R$). The disconnect time ($\tau_1$) is kept constant while each successive oxidation step is incremented by the same potential step ($\Delta E = E_{w2} - E_{w1}$). OPCV affords the possibility of collecting voltammetric data by performing a series of OCPA steps. OCPV is schematically illustrated in FIG. 5B. The top panel in the figure illustrates the pulse sequence; the bottom panel shows the current response. OCPV is implemented by first applying an oxidation potential ($E_{W1}$) and then incrementing this potential by a step ($\Delta E$), similar to other pulse voltammetric methods. To obtain voltammetric data, the potential of the oxidizing pulse ($E_{w1}$, $E_{w2}$, etc.) was varied, but the current was always measured on the reductive step at the OCP ($E_R$). The disconnect time ($\tau_1$) is kept constant while each successive oxidation step is, in a preferred embodiment, incremented by the same potential step ($\Delta E = E_{w2} - E_{w1}$). As the potential approaches the $E_{1/2}$, a larger fraction of the molecules in the SAM is oxidized; therefore, the magnitude of the faradaic current increases (FIG. 5B, bottom). Once the oxidizing potential step is sufficiently positive of the $E_{1/2}$, the observed instantaneous current remains unchanged, regardless of any additional increments in the oxidizing potential. The resulting output is similar to the steady state response observed for conventional pulse voltammetry at slow scan rates (Osteryoung and Osteryoung (1986) *Anal. Chem. Symp. Ser.*, 25: 3-12). For better S/N, the current observed in each step is integrated to yield the total charge (Q), which is then normalized to electrode area for ease of comparison between systems.

III. Evaluation of OCPA and OCPV Methods.

The efficacies of OCPA and OPCV were demonstrated using SAMs comprising two types of thiol-derivatized, redox-active molecules attached to gold: (1) an alkyl-ferrocene and (2) a Zn tetraarylporphyrin (see Example 1). We show that OPCA and OPCV permit the accurate measurement of the charge associated exclusively with the surface-bound redox species with very high signal quality in a very short time period.

We also evaluated the effect of the magnitude of the open circuit resistance on the dissipation of charging current by modifying the experiment slightly. Rather than disconnecting the counter electrode from the applied potential completely, a DPDT switch was used to connect the counter electrode to ground through a known resistance. This resistor provided a well-defined current path to ground during $\tau_1$. When a 2 GΩ resistor was placed between ground and the counter electrode, the time required to reach OCP decreased by 73% compared with the time required under "open" circuit conditions. Use of a 1 GΩ resistance yielded a still shorter time to reach OCP (decreased by 83%). In both cases, the OCPA method still measured a substantial amount of stored charge at long times, albeit diminished in magnitude. If the resistance was less than 10 MΩ, the decay to OCP was too fast to measure with this experimental arrangement and no current was measured. These data indicate that charging current is leaking from the counter electrode to ground once the cell is open-circuited.

IV. Practice of OCPA and OCPV.

In general, the methods of this invention are performed in the same manner as typical amperometric or voltammetric measurements, however, during the measurement, an electrode (the "charging" electrode) is disconnected (e.g., electrically decoupled) from the sample (e.g., from an electrochemical cell comprising the sample) to allow the cell to each an open circuit potential (OCP). The OCP is the potential at which no charging current flows through the external circuit of an electrochemical cell (Conway, et al. (1984) *J. Electroanal. Chem. Interfacial Electrochem.* 161: 39-49; Short and Shell (1985)*J. Phys. E*, 18: 79-87).

In the methods of this invention the open circuit potential of the electrochemical cell need not be exactly the potential at which zero current flows. An open circuit potential that allows a faradaic signal to be clearly distinguished from, e.g., capacitive/charging effects of the electrochemical cell is sufficient. In preferred embodiments, the open circuit potential is sufficient to result in a "background" signal that is less than 50%, preferably less than 20%, more preferably less than 10%, and most preferably less than 5%, or 1%, or 0.1% of the faradaic signal.

A) Disconnecting the Electrode

The electrode is typically disconnected (e.g., decoupled) for sufficient time ($\tau_1$) to allow the cell potential to decay to (or close to) the OCP. The cell is then reconnected (e.g., at a potential equal to or approximately equal to the OCP) and the resulting current, if such exists, is detected. The magnitude of the current is a measure of the oxidation state of said compound.

The electrode (circuit) can be disconnected in a number of different ways (rather than just using a switch or a relay in the path between the voltage source and the counter electrode). In certain preferred embodiments, the current path either has a high impedance route (i.e., the circuit is "open", and molecules stay oxidized (or reduced) and charge is retained) and a low impedance route (i.e., when the circuit is "closed" and the molecules are reduced (or oxidized)). The OCPA behavior of the molecules is affected by the magnitude of impedance (i.e., when the circuit is open, the greater the impedance, the longer charge is retained by the molecules, but it takes longer to discharge the capacitance. Also, one can place the "switch" after the working electrode and leave the reference connected, such that there is still a high impedance path between the potential and ground.

B) Potentiostats Optimized for OCPA and OCPV

Figure 1:
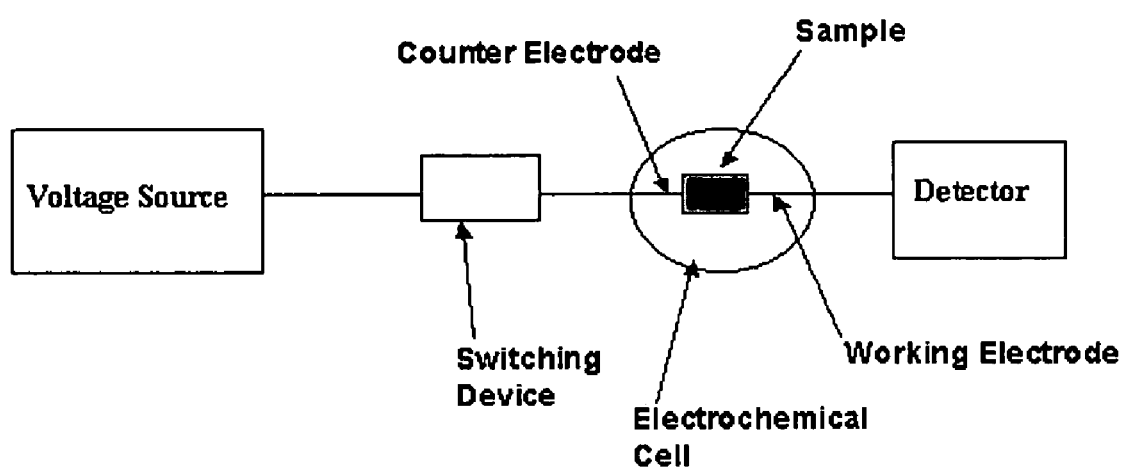
FIG. 1 schematically illustrates a potentiostat according to this invention.

FIG. 1 illustrates one preferred embodiment of a potentiostat used to implement the methods of this invention. A potential source is used connected to the material whose oxidation state is to be set and/or determined (the redox active material) through a switching device. In a preferred embodiment the redox active material, preferably together with two or more electrodes forms an electrochemical cell. The switching device permits the electrochemical cell to be electrically isolated from the voltage source. In certain embodiments, the voltage source can be used to set the oxidation state of the redox active material through a counter electrode. In preferred embodiments, a second electrode (e.g., a working electrode) electronically connects the redox active material to a detector that, e.g., permits measurement of a current.

Figure 2:
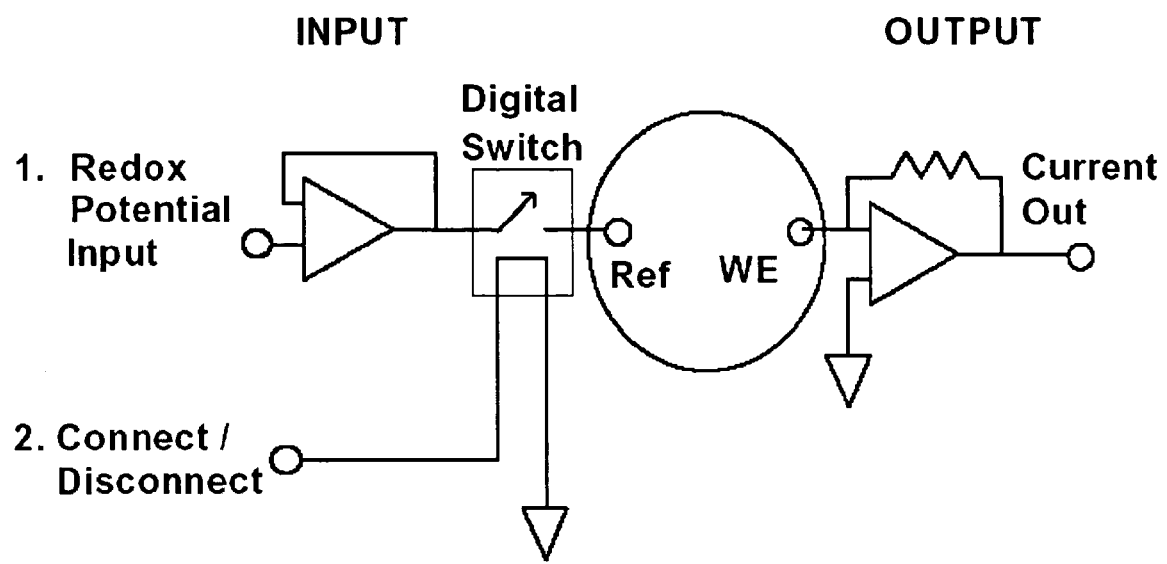
FIG. 2 illustrates a high-bandwidth potentiostat according to this invention. A two-electrode potentiostat was constructed with a high-bandwidth current amplifier using two high-bandwidth operational amplifiers, but the potential is applied though a voltage follower connected to the counter electrode via a fast switching mercury-wetted relay. The electrochemical cell could be open-circuited at the counter electrode using this switch with a rise-time of 500 ns.

In preferred embodiments, the potential control of the electrochemical cell is quite different from that found in a traditional potentiostat. As illustrated in FIG. 2, in one preferred embodiment, the potential is applied though a voltage follower (e.g., Burr-Brown OPA602), which is connected to a counter electrode via a fast switching device (e.g., a mercury-wetted relay). The electrochemical cell can be open-circuited at the counter electrode using this switching device, e.g., with a rise time of 1000 ns or less, preferably 500 ns or less, more preferably 250 ns or less. The potentials can be generated according to standard methods known to those of skill in the art. Such methods include, for example dedicated circuits (e.g., read/refresh/write circuits) and/or more generalized instrumentation (e.g., using LabVIEW). The current can also be collected through the potentiostat and, in preferred embodiments, is digitized.

V. Uses of OCPA and OCPV.

The methods of this invention can be used in a wide variety of contexts. For example, many electrochemical methods have been used to study the redox properties of electroactive molecules in solution or immobilized on electrode surfaces (Creager and Wooster (1998) *Anal. Chem.*, 70: 4257-4263; Weber and Creager (1994) *Anal. Chem.*, 66: 3164-3172; Forster and Faulkner (1994) *Am. Chem. Soc.* 116: 5453-5461; Forster (1996) *Analyst* (Cambridge, U. K.), 121: 733-741; Forster et al. (2000) *J. Phys. Chem. B*, 104: 4425-4432; Kertesz et al. (1999) *Electrochim. Acta*, 45: 1095-1104; Palecek et al. (1997) *Electroanalysis*, 9: 990-997).

The methods of this invention can also be used in a variety of detection systems, e.g., to detect and/or quantify one or more analytes (e.g., nucleic acids, proteins, porphyrinic biomolecules, and other redox-active materials). Such sensor systems typically utilize a capture ligand (e.g., a protein, nucleic acid, antibody, lectin, etc.) to capture an analyte and immobilize that analyte on a surface resulting in an electrical connection between the analyte and an electrode. Electrochemical methods (e.g., amperometry, voltammetry, etc.) are then used to detect and/or to, quantify the analyte at the electrode (see, e.g., U.S. Pat. Nos. 5,958,215 and 5,650,061).

There is great interest in the utilization of electrochemical detection methods at arrays of biosensor elements (Cheng et al. (1998) *Nature Biotechnology*, 16: 541-546). Such arrays can be used to simultaneously detect/quantify multiple analytes (e.g., different proteins, different species of DNA, etc.) and are well suited to "lab on a chip" applications.

Thus, in certain embodiments, this invention contemplates the use of the methods described herein with electrochemical sensors. The sensors typically comprise an electrochemical cell that can capture one or more target analytes (e.g., nucleic acids, peptides, sugars, fats, carbohydrates, etc.). The specificity of the sensor can be achieved with the use of a ligand (e.g., an antibody (full, antibody fragment, single chain antibody, etc., a nucleic acid, a lectin, a carbohydrate, and the like) that specifically binds to or hybridizes with the target analyte. The binding event is detected by a change in redox state or redox activity of the sensor and this is measured using an electrochemical measurement (e.g., OCPV, OCPA, etc.), as described herein.

In addition, arrays of redox elements forming arrays of electrochemical cells can be used as molecular memories (see, e.g., U.S. Pat. Nos. 6,272,038, 6,212,093, 6,208,553, and international patent applications WO 01/51188 and WO 01/03126). In preferred embodiments, the electrochemical cells ("storage cells") include a fixed electrode electrically coupled to a "storage medium" having a multiplicity of different and distinguishable oxidation states where data is stored in the (preferably non-neutral) oxidation states by the addition or withdrawal of one or more electrons from said storage medium via the electrically coupled electrode.

Figure 7:
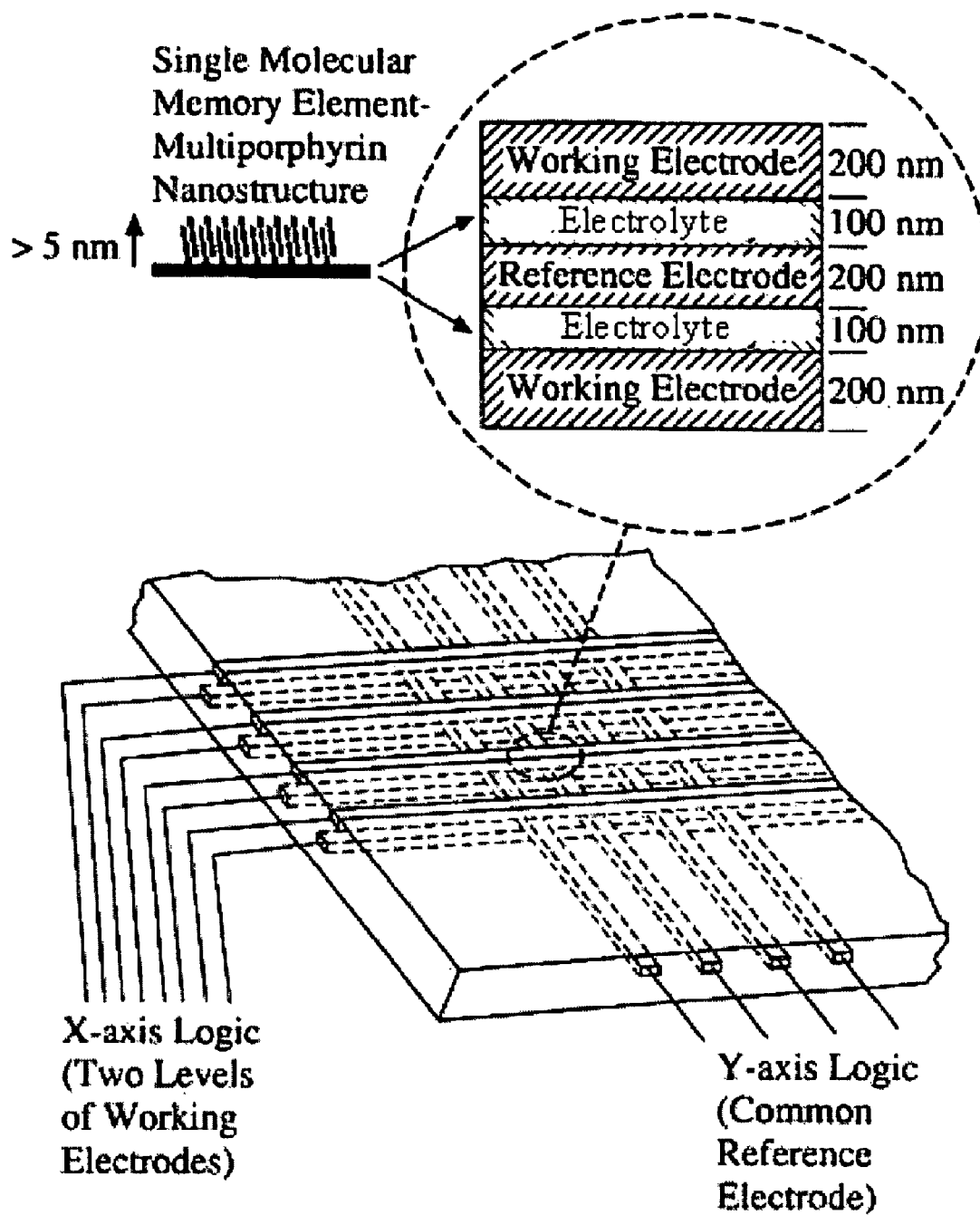
FIG. 7 schematically illustrates one basic molecular memory unit "storage cell".

FIG. 7 schematically illustrates a basic molecular memory unit "storage cell", e.g., as described in WO 01/03126. The basic memory device, a "storage cell" 100 comprises a working electrode 101 electrically coupled to a storage medium 102 comprising a multiplicity of storage molecules 105. The storage cell optionally includes an electrolyte 107 and a reference electrode 103. The storage medium has a multiplicity of different and distinguishable oxidation states, preferably a multiplicity of different and distinguishable non-neutral oxidation states, and can change oxidation (charge) state when a voltage or signal is applied thereby adding or removing one or more electrons.

Because molecular dimensions are so small (on the order of angstroms) and individual molecules in molecular memory devices (arrays of electrochemical (storage) cells) store multiple bits, such molecular memory devices offer remarkably high storage densities (e.g., $>10^{15}$ bits/cm$^3$).

In certain embodiments, the memory elements comprising the memory devices of this invention are fabricated using "moleholes". In certain embodiments, a "molehole" comprises a two or more arrays of conductors or semiconductors (e.g., electrodes) separated from each other vertically (e.g., by a dialectric, insulator, etc.) so that the conductors overlap each other at least one point. Within one or more intersection point of an upper and lower electrode (e.g., top and bottom interconnect) a well is fabricated. This well penetrates the electrodes, so that the electrodes form a portion of the side and/or bottom of the well.

Storage molecules (e.g., porphyrinic macrocycles) are attached to one or more of the exposed conductor surfaces in the wells. Each well can then function as an electrochemical cell permitting electrochemical measurements of the bound molecules. The fabrication and use of such "moleholes" is described in detail in copending application U.S. Ser. No. 10/046,499, filed on Oct. 26, 2001.

As the density of these storage devices (or other electrochemical cell (e.g., sensor) arrays) arrays increase, two compounding problems manifest. High densities of sensors (electrochemical cells) require that each sensor element (cell) becomes smaller (ultimately, to micron dimensions); hence, the signal amplitude (proportional to sensor/cell area) also decreases. As the number of sensor elements increases, the time per measurement typically also decreases proportionately, thereby increasing measurement (read) bandwidth. The combination of these two effects leads to a situation where less signal must be measured with a wider bandwidth, leading to signal to noise (S/N) problems. The methods of this invention, by decoupling charging currents from faradaic currents dramatically improve S/N ratios and are particularly well suited to use with arrays of electrochemical cells.

The methods of this invention are particularly useful where the redox active material to be measured and the electrochemical cell comprising the redox active material meet certain conditions. In particular, the methods of this invention are particularly preferred where the open circuit potential (OCP) is well defined and can be readily determined. In addition it is helpful if the open circuit potential is at an analytically useful potential (e.g., in the case of molecular memories described herein at a reducing potential). It is also desirable that the compositions/molecules comprising the redox active material remain oxidized (or reduced) as the electrochemical cell potential decays to the OCP under open-circuit conditions. Finally, it is desirable that the redox active material remain oxidized (or reduced) and be readily reduced (or oxidized) upon reconnection of the circuit.

A wide number of redox active materials store charge over a time frame well suited to detection using the methods of this invention. Such redox-active materials include, but are not limited to, various analytes (e.g., biomolecules, various environmental pollutants, and the like) that it is typically desired to detect using a "biosensor". In addition, materials used in molecular memory devices (e.g., various self-assembled monolayers (SAMs) as are described in WO 01/03126). Particularly preferred redox-active materials include, but are not limited to porphyrinic macrocycles, most preferably porphyrins. The porphyrins can be arranged in a wide variety of configurations, e.g., linear polymers, branched polymers, arrays, etc. (see e.g., WO 01/03126).

EXAMPLES

The following examples are offered to illustrate, but not to limit the claimed invention.

Example 1

Open Circuit Potential Amperometry and Voltammetry of Surface-Bound Redox Species In this example, a new method is described to temporally dissociate the faradaic current from the background current associated with reading the charge of a redox-active SAM. This method, designated open circuit potential amperometry (OCPA), effectively reads the charge of the redox species bound to the electrode surface, while discriminating against both charging currents and amperometric signals that arise from diffusion-based species in solution. Voltammetric data can also be obtained using OPCA. In the voltammetric method, designated open circuit potential voltammetry (OPCV), a series of OCPA steps is performed in which the oxidizing potential is successively incremented, while the reading potential is maintained at the OCP. The efficacies of OCPA and OPCV are demonstrated using SAMs two types of thiol-derivatized, redox-active molecules attached to Au, (1) an alkyl-ferrocene and (2) a Zn tetraarylporphyrin. The studies show that both methods permit the accurate measurement of the charge associated exclusively with the surface-bound redox species with very high signal quality in a very short time period.

Experimental Section

Construction of a High-Bandwidth Potentiostat

A two-electrode potentiostat was constructed with a conventional high-bandwidth current amplifier using two high-bandwidth operational amplifiers (FIG. 2). The first stage is a current-feedback inverting amplifier (Burr-Brown OPA644) and the second stage is an inverting voltage-feedback amplifier (Analog-Devices AD744), which together provide an overall amplification of 2020. The frequency response of this amplifier is flat to 1 MHz. The potential control of the electrochemical cell is quite different from that found in a traditional potentiostat. The potential is applied though a voltage follower (Burr-Brown OPA602), which is connected to the counter electrode via a fast switching mercury-wetted relay (Aleph International Corp.). The electrochemical cell could be open-circuited at the counter electrode using this switch with a rise time of 500 ns. The potentials were generated in LabVIEW and applied through the potentiostat. The current was also collected through the potentiostat and digitized at a rate of 5 MHz (National Instruments PCI-6110E data acquisition board).

Formation and Redox Characteristics of the SAMs

Figure 3A:
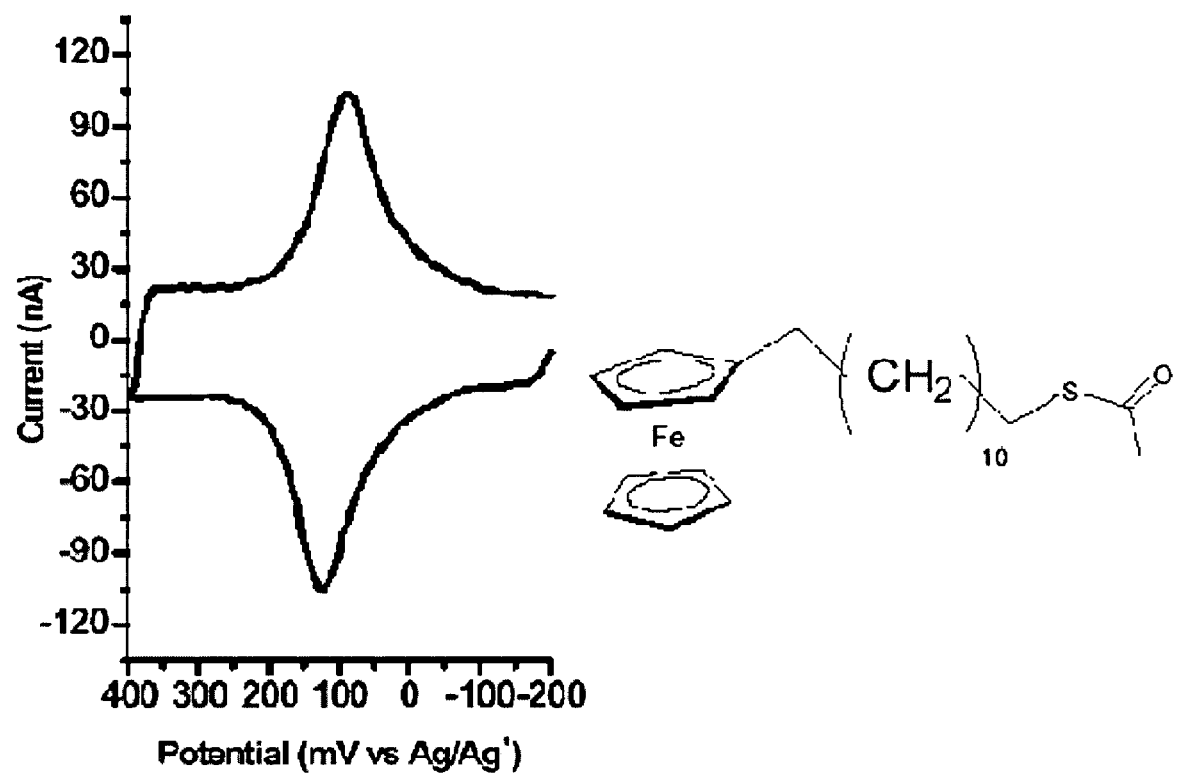
FIGS. 3A and 3B illustrate structures and voltammetry of $C_{12}Fc$ (FIG. 3A) and ZnP (FIG. 3B). Thiol-derivatized alkyl ferrocene ($C_{12}F$) and Zn tetraarylporphyrin (ZnP) were synthesized as the S-acetyl derivatives. The cyclic voltammograms (scan rate 100 V/s) of the C12Fc and ZnP SAMs were obtained using 10 μm diameter Au ball microelectrode immersed in dried, distilled $CH_2Cl_2$ containing 0.1 M $Bu_4NPF_6$. All potentials are recorded vs $Ag/Ag^+$.
Figure 3B:
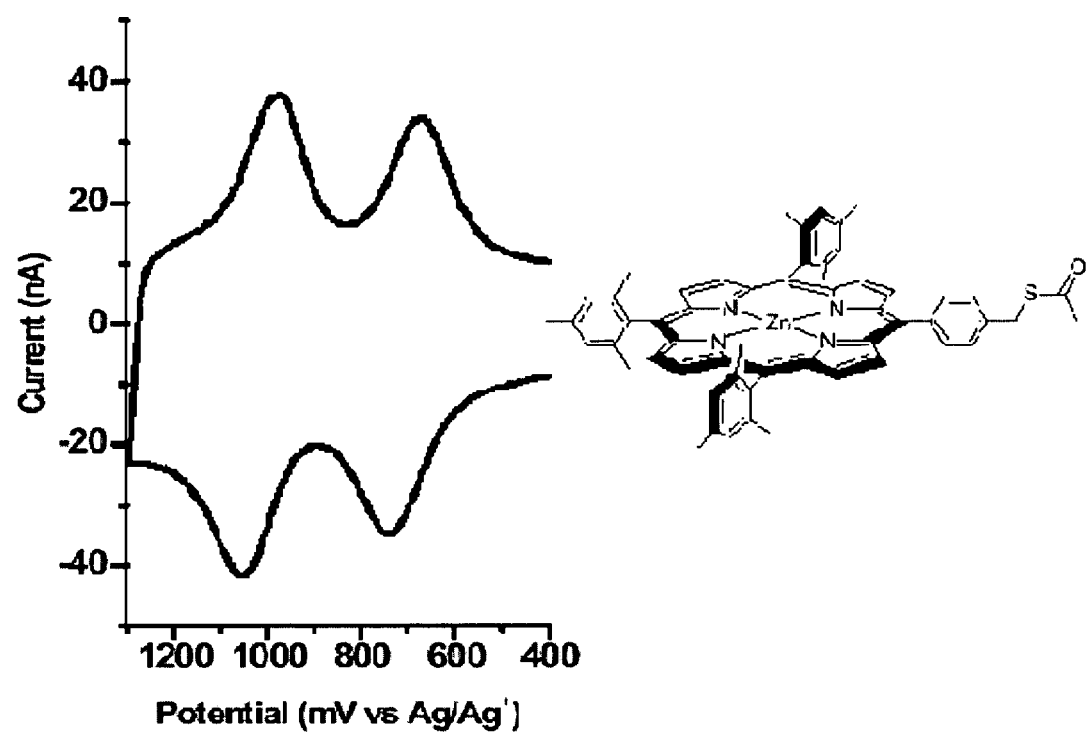

The structures of the thiol-derivatized alkyl-ferrocene ($C_{12}F$) and Zn tetraarylporphyrin (ZnP) are shown in FIG. 3. These molecules were synthesized as previously described (Gryko et al. (1999) *J. Org. Chem.*, 64: 8635-8637; Creager and Rowe (1994) *J. Electroanal. Chem.*, 370: 203-211) and prepared as the S-acetyl derivatives (see, e.g., WO 01/03126). The S-acetyl protecting group has been shown to undergo facile cleavage upon exposure to gold (Au) (Tour et al. (1995) *J. Am. Chem. Soc.*, 117: 9529-9534; Gryko et al. (1999) *J. Org. Chem.*, 64: 8635-8637). The Au ball working electrode was prepared from 5 μm diameter Au wire sealed in soft glass (Creager et al. (1999) *J. Am. Chem. Soc.*, 121: 1059-1064). Initially a ~500 μm segment of the wire was protruding from the end of 1 mm i.d. soft glass tubing. When exposed to a flame the glass forms a tight seal around the Au while the wire exposed directly to the flame melts into a ball that terminates at the surface of the glass. The electrode was then cooled in a stream of nitrogen and used immediately. The ball was found to have an average diameter of 10 μm$^2$. Finally, the electrode was placed in a 2 mg/ml solution of $C_{12}F$ or ZnP for 20 min. and sonicated for an additional 1 min. The electrode was removed and rinsed with distilled $CH_2Cl_2$. All electrochemical potentials are vs Ag/Ag$^+$ and recorded in dried, distilled $CH_2Cl_2$ containing 0.1 M Bu$_4$NPF$_6$. As shown in FIG. 3, the $C_{12}F$ SAM exhibits a single oxidative wave at $E_{1/2}$=0.25 V; the ZnP SAM exhibits two oxidative waves at $E_{1/2}(1)$=0.73 V and $E_{1/2}(2)$=1.05 V.

Determination of Open Circuit Potential (OCP)

The OCP (Conway, et al. (1984) *J. Electroanal. Chem. Interfacial Electrochem.* 161: 39-49; Short and Shell (1985) *J. Phys. E*, 18: 79-87) of the electrochemical cell was determined empirically in a series of experiments performed as follows (FIG. 4A, FIG. 4B): (1) The potential was poised at an arbitrary value where no faradaic current is expected. (2) The circuit was then opened at the counter electrode for a sufficient time ($\tau_1$) to discharge the capacitance of the electrodes in the electrochemical cell. (3) A potential was then applied to the counter electrode, the circuit was closed, and the resulting current was monitored. If the applied potential is not the OCP, charging current flows to create an electric field identical to that generated externally. This process was repeated at a series of different voltages to determine the potential at which no current flows, which, by definition, is the OCP.

Open Circuit Potential Amperometry (OCPA)

OCPA is schematically illustrated in FIG. 5A. The top of panel A in the figure illustrates the pulse sequence; the lower panel shows the current response. Initially, an oxidizing potential ($E_W$) was applied to the system through the closed switch in the potentiostat. The switch was then opened to disconnect the counter electrode from the electrochemical circuit for a specified time ($\tau_1$). After the electrochemical cell decayed to the OCP (which is a reducing potential) the switch is closed and the circuit was reconnected to an externally applied potential equal to the OCP ($E_R$). The oxidized SAM is immediately reduced, and the resulting faradaic current was recorded (FIG. 5, panel A, bottom).

Determination of Open Circuit Charge Retention

The magnitude of charge retention in the oxidized SAM can be determined with OCPA as is also illustrated schematically in FIG. 5A. Charge retention is measured by successively changing the disconnect time ($\tau_1$, $\tau_2$, etc.), which is the interval between the oxidation of the SAM and the consequent reduction of the oxidized SAM at the OCP. The current observed is directly proportional to the fraction of in the SAM that are retained in the oxidized state during the storage cycle. We have previously shown that the decay in the charge (the integrated current) for porphyrin SAMs fits a first-order rate law, allowing the calculation of a half-life ($t_{1/2}$) for the process.

Open Circuit Potential Voltammetry (OCPV)

OPCV affords the possibility of collecting voltammetric data by performing a series of OCPA steps. OCPV is schematically illustrated in FIG. 5B. The top panel in the figure illustrates the pulse sequence; the bottom panel shows the current response. OCPV is implemented by first applying an oxidation potential ($E_{w1}$) and then incrementing this potential by a step ($\Delta E$), similar to other pulse voltammetric methods. To obtain voltammetric data, the potential of the oxidizing pulse ($E_{w1}$, $E_{w2}$, etc.) was varied, but the current was always measured on the reductive step at the OCP ($E_R$). The disconnect time ($\tau_1$) was kept constant while each successive oxidation step was incremented by the same potential step ($\Delta E = E_{w2} - E_{w1}$). In our experiments, each step was applied to the reference electrode for 20 ms and followed by disconnect time ($\tau_1$) of 15 s. As the potential approaches the $E_{1/2}$, a larger fraction of the molecules in the SAM is oxidized; therefore, the magnitude of the faradaic current increases (FIG. 5B, bottom). Once the oxidizing potential step is sufficiently positive of the $E_{1/2}$, the observed instantaneous current remains unchanged, regardless of any additional increments in the oxidizing potential. The resulting output is similar to the steady state response observed for conventional pulse voltammetry at slow scan rates (Osteryoung and Osteryoung (1986) *Anal. Chem. Symp. Ser.*, 25: 3-12). For better S/N, the current observed in each step is integrated to yield the total charge (Q), which is then normalized to electrode area for ease of comparison between systems.

Results and Discussion

Many electrochemical methods have been used to study the redox properties of electroactive molecules immobilized on electrode surfaces (Creager and Wooster (1998) *Anal. Chem.*, 70: 4257-4263; Weber, K.; Creager, S. E. Anal. Chem. 1994, 66, 3164-3172; Forster and Faulkner (1994) *Am. Chem. Soc.* 116: 5453-5461; Forster (1996) *Analyst* (Cambridge, U. K.), 121: 733-741; Forster et al. (2000) *J. Phys. Chem. B*, 104: 4425-4432; Kertesz et al. (1999) *Electrochim. Acta*, 45: 1095-1104; Palecek et al. (1997) *Electroanalysis*, 9: 990-997). While many of these studies were conducted to obtain fundamental information about electron transfer and physical phenomena involved in redox processes of the surface-confined species, there is increased interest in the rapid quantitation of redox species at surfaces. This is particularly true in the field of DNA (and other biomolecular) sensors, where there is much interest in the utilization of electrochemical detection methods at arrays of biosensor elements (Cheng et al. (1998) *Nature Biotechnology*, 16: 541-546). As the density of these arrays increase, two compounding problems are manifested. Higher densities of sensors require that each sensor element becomes smaller (ultimately, to micron dimensions); hence, the signal amplitude (proportional to sensor area) also decreases. As the number of sensor elements increases, the time per measurement must also decrease proportionately, which necessitates that the bandwidth of the measurement increases. The combination of these two effects leads to a situation where less signal must be measured with a wider bandwidth, leading to severe S/N problems.

Modulation techniques have been used very effectively in a number of circumstances to improve signal quality of surface immobilized redox species (Creager et al. (1999) *J. Am. Chem. Soc.*, 121: 1059-1064). In AC voltammetry, a potential ramp is applied to the electrode (typically 10 to 50 mV/s), a small amplitude sine wave (always less than 50 mV; usually 10 mV (Eccles (1991) *Crit. Rev. Anal. Chem*, 22: 345-380)) is superimposed onto the linear ramp, and the signal is measured at the fundamental or second harmonic frequency using a lock-in amplifer. Small amplitude modulations are used exclusively to ensure that the faradaic response remains essentially linear (Eccles (1991) *Crit. Rev. Anal. Chem*, 22: 345-380). Thus, these measurements are limited to either the fundamental frequency or lower-order harmonics. The scan rate is determined by the slope of the linear ramp; the time of analysis typically varies between 20 to 200 s. Because the potential is modulated at one hundred to one thousand times the fundamental frequency of the ramp, modulation frequencies are typically in the tens to hundreds of hertz. AC voltammetry has been used to study the kinetics of monolayers of redox-active molecules tethered to electrode surfaces via alkane thiols (Creager and Wooster (1998) *Anal. Chem.*, 70: 4257-4263) or molecular-scale wires (Creager et al. (1999) *J. Am. Chem. Soc.*, 121: 1059-1064). While this approach is extremely useful in the determination the kinetic parameters governing these systems, there are practical limitations to the analytical implementation of the approach. In particular, the technique does not completely discriminate against charging currents under conditions of low surface coverage or when fast measurements are required (e.g., fast scan rates (Creager et al. (1999) *J. Am. Chem. Soc.*, 121: 1059-1064)).

Chronoamperometry of Redox SAMs

Chronoamperometry has been utilized to rapidly interrogate the redox properties of surface-bound molecules (Forster (1996) *Analyst* (Cambridge, U. K.),121: 733-741; Forster et al. (2000) *J. Phys. Chem. B*, 104: 4425-4432; Kertesz et al. (1999) *Electrochim. Acta*, 45: 1095-1104; Sevilla et al. (1998) *Electroanal. Chem.*, 442: 107-112); however, it is difficult to dissociate the current that arises from the redox processes in a monolayer from the capacitive current at the electrode interface. Pulse methods can discriminate the faradaic current arising from redox processes of diffusing species from the charging current in the time domain because charging currents decay much more rapidly than the diffusion-limited faradaic current ($\exp(-t/RC)$ vs $t^{-1/2}$, respectively). However, these methods do not totally discriminated the faradaic current from the charging current. In addition, most of the signal is discarded because sampling must be done late in the pulse cycle.

Figure 6A:
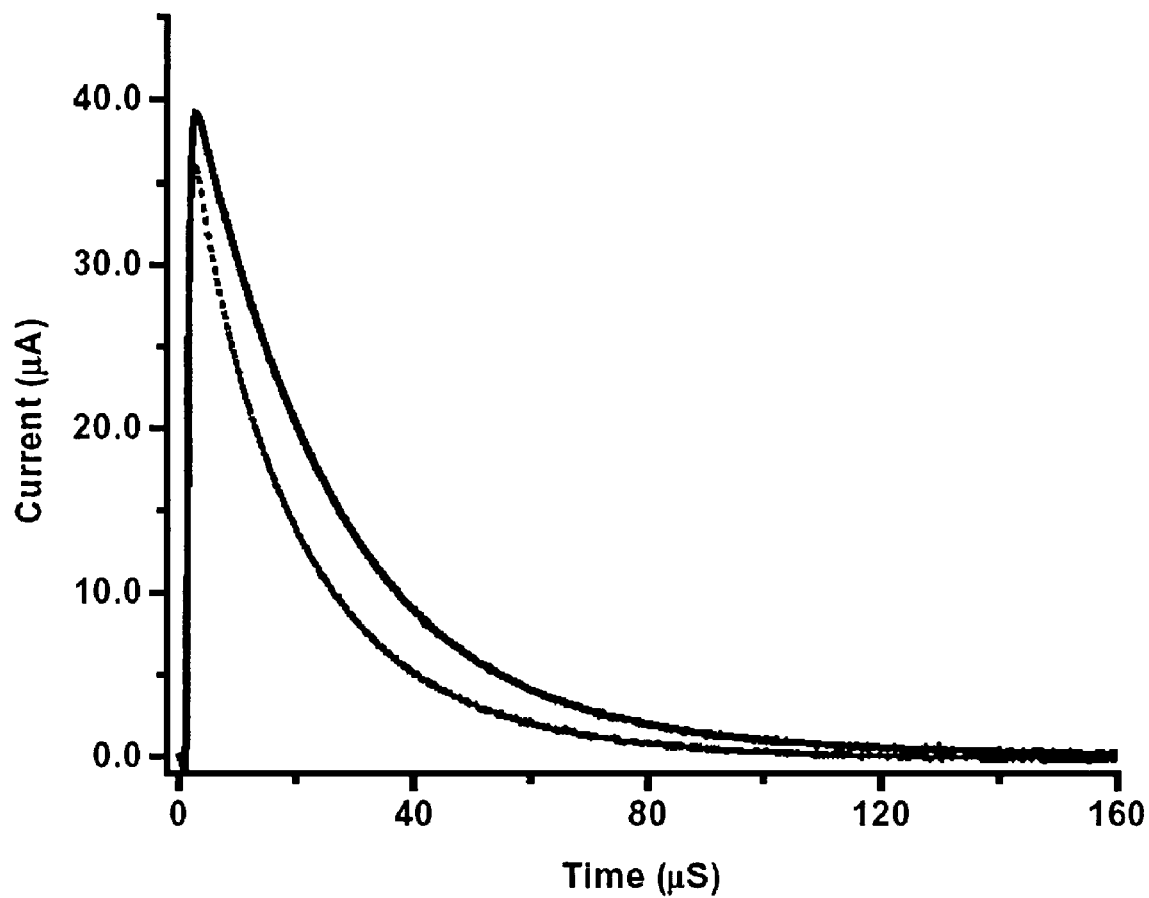
FIGS. 6A, 6B, 6C, and 6D illustrate OCPA of the $C_{12}F$ and ZnP SAMs. All experiments were performed on a 10 µm diameter Au ball, using the two-electrode, 5-MHz bandwidth potentiostat. Chronoamperometry: Standard chronoamperometry was performed at (FIG. 6) $C_{12}Fc$ SAM from 0-300 mV (dashed line) and from 300-0 mV vs Ag/Ag$^+$ (solid line) and (FIG. 6) ZnP SAM from 300-0 mV (dashed line) and from 800-500 mV vs Ag/Ag$^+$ (solid line). The dashed traces in the two panels show the current observed when the potential is stepped in a range where the SAM is not redox active (i.e., where no faradaic current flows); the solid line represents a step that contains both faradaic and charging currents. OCPA: The same SAMs on the same electrodes were examined with OCPA at (FIG. 6C) $C_{12}Fc$ SAM; oxidized at $E_w$=+300 mV vs Ag/Ag$^+$ for 20 ms prior to disconnection. The reductive current was measured after reconnection of the counter electrode at the OCP ($E_R$=−400 mV vs Ag/Ag$^+$, determined as shown in FIG. 4) after a disconnect time ($\tau_1$) of 100 s, and (FIG. 6D) ZnP SAM; oxidized at $E_W$=+800 mV vs Ag/Ag$^+$ for 20 ms prior to disconnection. The reductive current was measured after reconnection of the counter electrode at the OCP (ER=+125 mV vs Ag/Ag+) with a disconnect time ($\tau_1$) of 100 s. As in the previous panels, the dashed traces in the two panels show the current observed when the SAM is not redox active (i.e., where no faradaic current flows); the solid line represents a step that contains primarily faradaic current.
Figure 6B:
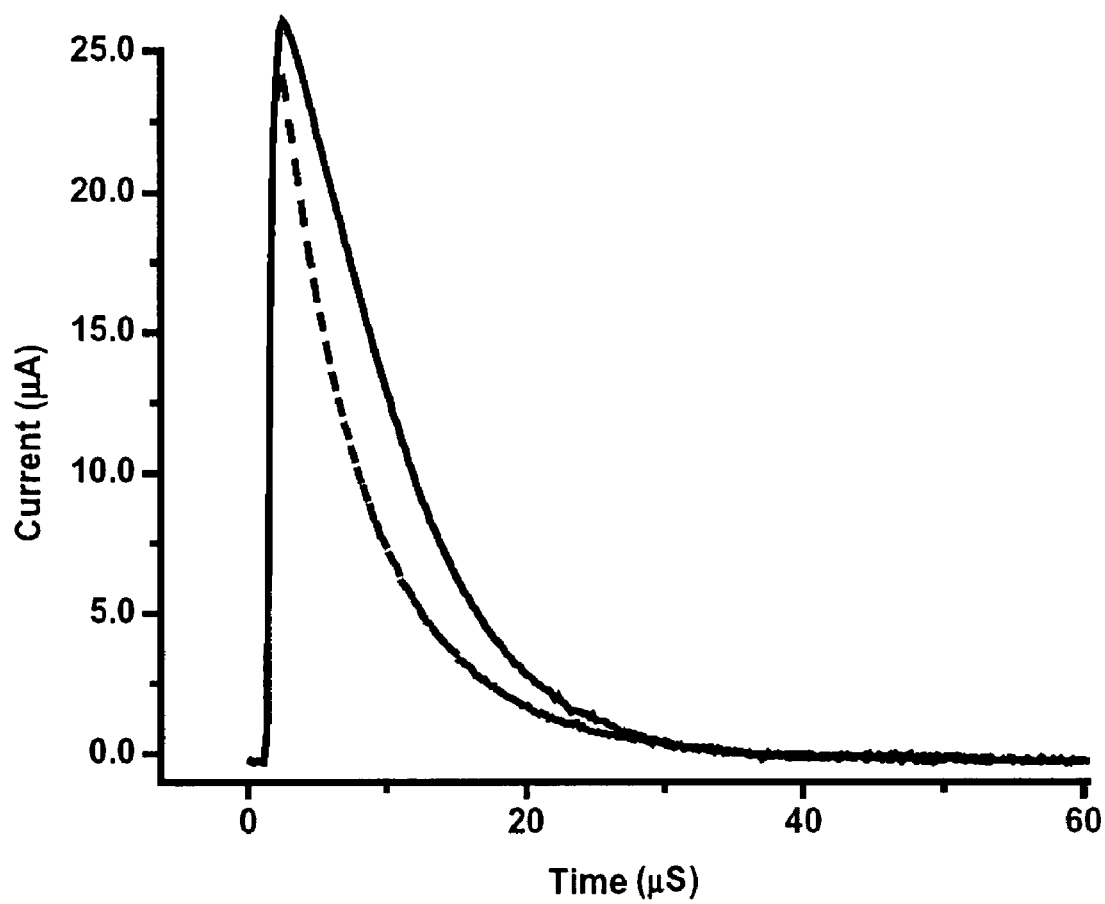

The problems associated with conventional chronoamperometry are illustrated in FIG. 5, which shows the transient current observed when a 300 mV potential step is applied to the $C_{12}F$ (FIG. 6A) and ZnP (FIG. 6B) SAMs. The dashed traces in the two panels show the current observed when the potential is applied at a value where no faradaic current occurs. Consequently, the potential pulse produces only a background current that arises primarily from charging the electrochemical double-layer capacitance. The solid traces show the current produced when the potential step is set at a potential 150 mV more positive than the $E_{1/2}$ of the SAM. This signal contains both the faradaic current and a background current. As can be seen, the faradaic current resulting from oxidation of the SAMS has the same time course as the charging current. This result indicates that the rate of electron transfer for $C_{12}F$ and ZnP is much faster than the RC time constant of the electrochemical cell (Forster et al. (2000) *J. Phys. Chem. B*, 104: 4425-4432). Thus, the instantaneous faradaic current arising from the redox process can never be well discriminated from the instantaneous charging current that arises from the capacitive properties of the electrode. This situation becomes particularly problematic when dealing with dilute monolayers or electrodes with less than 100% monolayer coverage.

Properties of OCP Methods

The signal quality of the measurement of redox properties of an immobilized redox-active molecule, i.e., the ratio of faradaic to charging currents, can be significantly improved if the faradaic current can be temporally decoupled from the charging current. Temporal dissociation of the two processes is possible if the surface-bound redox species maintain their redox state (for some finite period of time) on the electrode under open circuit conditions (i.e., it is possible to read the faradaic current after the electrode potential has changed). This measurement requires (1) that the OCP is well-defined, can be readily determined, and is at an analytically useful (i.e., in this case, reducing) potential; (2) that the molecules in the SAM remain oxidized as the electrochemical cell potential decays to the OCP under open-circuit conditions; and (3) that the molecules that remain oxidized in the SAM are readily reduced upon reconnection of the circuit. As will be shown below, the $C_{12}F$ and ZnP SAMs satisfy these conditions.

Determination of OCP

Figure 4C:
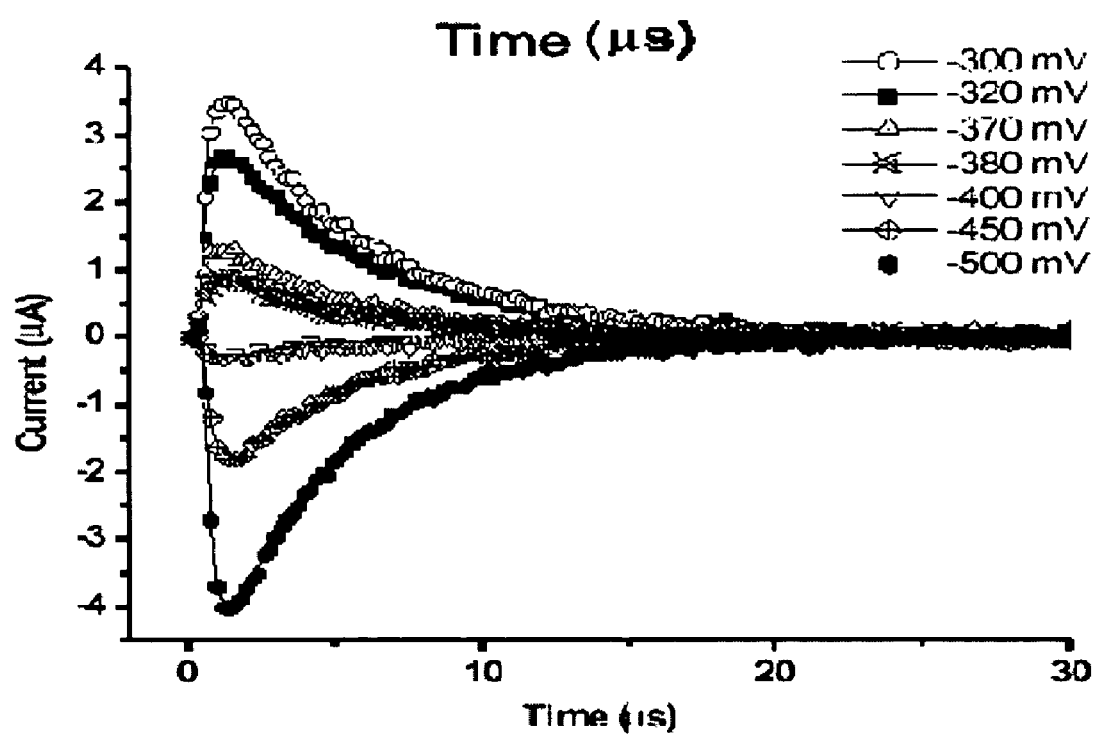

The OCP is the potential at which no charging current flows through the external circuit of an electrochemical cell (Conway, et al. (1984) *J. Electroanal. Chem. Interfacial Electrochem.* 161: 39-49; Short and Shell (1985) *J. Phys. E*, 18: 79-87). The empirical determination for the OCP of the $C_{12}F$ and ZnP SAMs is shown in FIG. 4C. Each of the current transients shown in the figure represents exclusively the charging current observed upon with reconnection of the electrochemical cell. Only charging current is observed because the potential steps are less than the $E_{1/2}$ of the SAMs. The OCP is the potential at which no current flows. The electrochemical cell can be connected and disconnected at the OCP at any time without the observation of any current. The value of the OCP depends greatly on the composition of the SAM. The $C_{12}F$ SAM has an experimentally determined OCP of −400 mV vs. Ag/Ag$^+$, whereas the ZnP SAM has an OCP of +100 mV (under identical solution conditions). Note also that in both cases, the OCP is more negative than the $E_{1/2}$ of the redox species immobilized to the surface.

OCPA of Redox SAMs

OCPA is qualitatively similar in many ways to conventional chronoamperometry; however, OCP amperometric methods differ in that measurement of the faradaic current is temporally dissociated from the charging current. This is accomplished by allowing the electrochemical cell to reach the OCP prior to the amperometric measurement (FIG. 5A). Thus, after initial oxidation of the monolayer, the circuit is left open for a long enough time ($\tau_1$) to allow the cell potential to decay to the OCP. When the circuit is reconnected (to an externally applied potential equal to the OCP; ER in FIG. 5A), molecules in the SAM that have remained in an oxidized state are immediately reduced, and the resulting faradaic current can be measured in the absence of charging current.

Figure 8A:
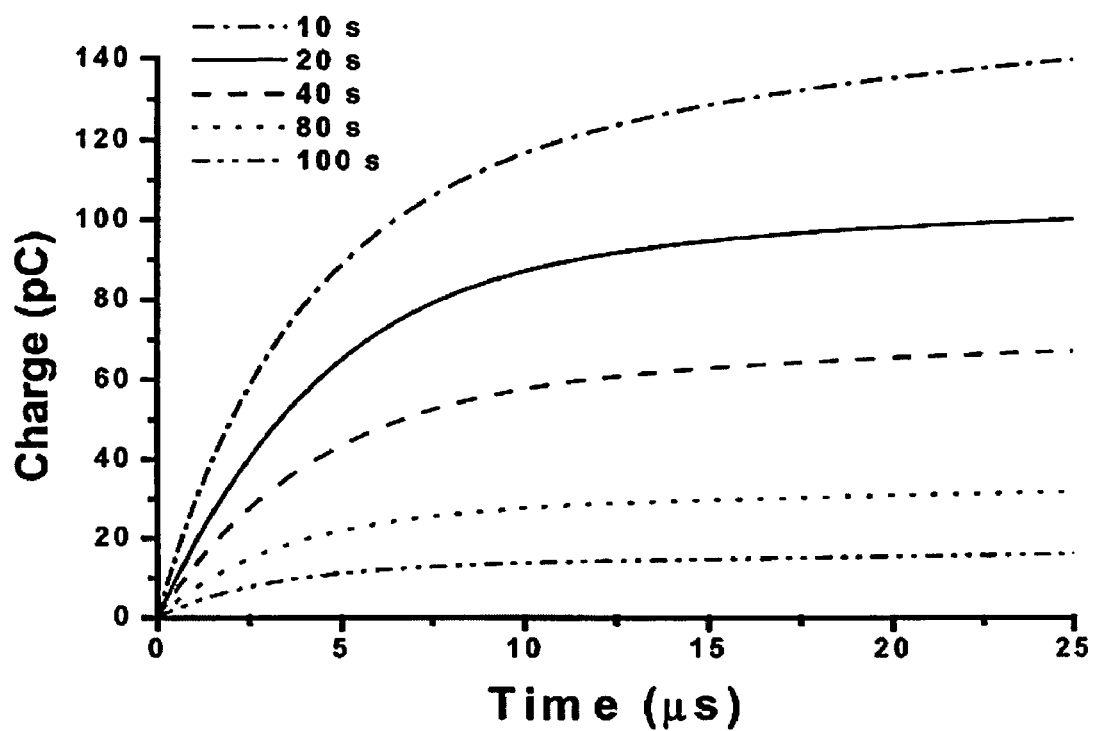
FIGS. 8A and 8B illustrate integration of OCPA current transients as a function of disconnect time ($\tau_1$). OCPA was performed for C12 Fc and ZnP SAMs as described in FIG. 6. The instantaneous current was digitally integrated as a function of time and recorded as the instantaneous charge normalized to electrode area. The disconnect time ($\tau_1$) was varied from 1 to 100 s for the $C_{12}Fc$ SAM (electrode area ~2500 µm$^2$.

A SAM of thiol-derivatized Zn-tetraarylporphyrins (ZnP) is an ideal molecule for analysis with OCPA. The current corresponding to the reduction of singly-oxidized ZnP molecules in the SAM is observed after the circuit is disconnected for 100-s at a 25-micron diameter disk electrode (FIG. 8A). This translates to retention of almost 66% of the charge in the singly-oxidized ZnP monolayer in that time period (Table 1). Previously, we have shown that the decay in the observed charge versus disconnect time fits a first-order rate law with extremely high fidelity, allowing the calculation of a charge retention half-life ($t_{1/2}$) for the process. The charge retention half-life is extremely dependent on the nature of the molecule, and as such, is an important property that must be characterized for each analyte.

TABLE 1

Charge retention characteristics of $C_{12}$Fc and ZnP SAMs.

| Redox Process | QCV$^a$ pC | $Q_0^b$ ($\tau_1$ = 0s) pC | $Q_0^b$ ($\tau_1$ = 10s) pC | $Q_0^b$ ($\tau_1$ = 100s) pC | $t_{1/2}^b$ s | $Q_{DL}^c$ (CA) pC | $Q_{BKGD}^d$ (OCPA) pC |
|---|---|---|---|---|---|---|---|
| $C_{12}F^+ \rightarrow C_{12}F$ | 162 | 168 | 140 | 16 | 31 s | 714 | 1.2 |
| ZnP$^+$→ZnP | 29 | 33 | 32 | 22 | 167 | 154 | 0.74 |
| ZnP$^{2+}$→ZnP | 56 | 54 | 53 | 32 | 254 | — | — |

Figure 6C:
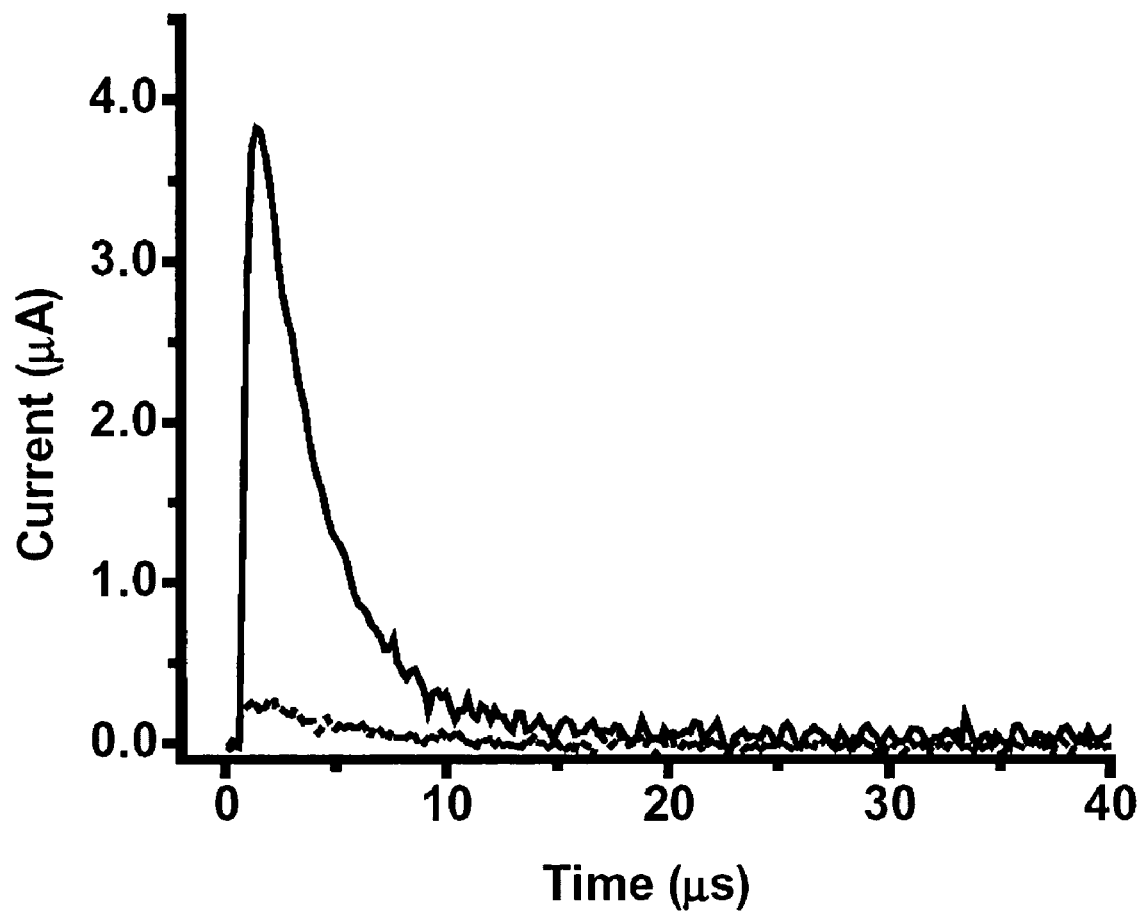
Figure 6D:
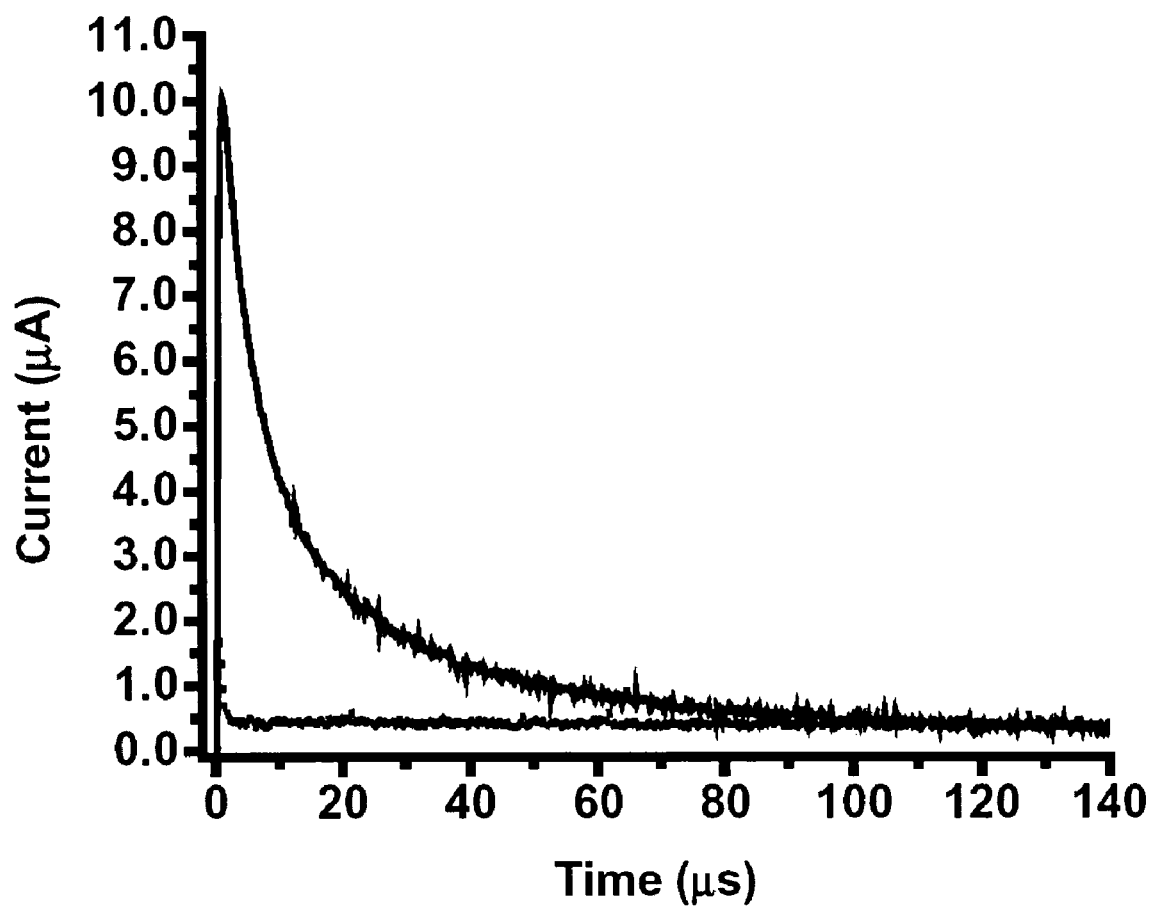

$^a$Q(CV), the integrated charge obtained from cyclic voltammetry, was obtained by digitally integrating the current under each peak obtained with cyclic voltammetry at 100 V s-1 (see FIG. 3)
$^b$Q$_0$, the charge at t = 0s, and t$^{1/2}$, the charge retention half-life, were determined by fitting the decay in the observed charge Q($\tau$), 25 µs integration time), vs. disconnect time ($\tau_1$) to a first order rate law.
$^c$Q$_{DL}$(CA), the integrated charging current obtained from chronoamperometry, was obtained by digitally integrating the current under each transient from 0-300 mV (160 µs integration time, see dotted lines, FIGS. 6A and 6B).
$^d$QBKGD(OCPA), the integrated background current obtained in OCPA, was obtained by digitally integrating the current under each transient when each SAM was in the reduced state prior to the OCPA measurement (25 µs integration time, see dotted lines, FIGS. 6C and 6D).

Figure 8B:
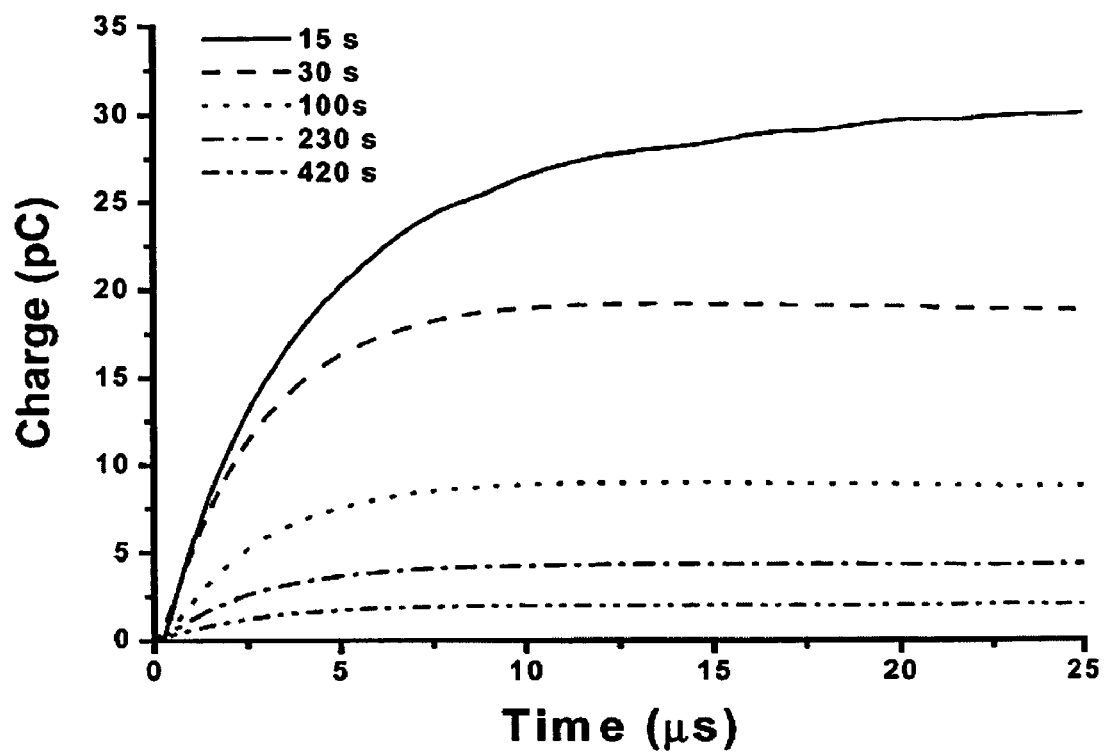

While the charge retention half-life of a $C_{12}F$ SAM is much shorter than ZnP SAM, there is a much larger initial charge density (Table 1). This scales with the size of the molecule in the monolayer, and is another parameter that can affect the total sensitivity of the measurement. Thus, even though the $C_{12}F$ SAM has a much higher initial charge density, the same residual charge is observed after 100 s, since it undergoes much faster charge dissipation (FIG. 8B). The current observed for OCPA of the $C_{12}F$ SAM at the same disconnect time (100 s) is almost an order of magnitude smaller than that observed for the ZnP SAM (Table 1). The $C_{12}F$ SAM loses approximately 91% of its original charge during this time, while less than 17% of the charge of the ZnP is lost in the same time interval. The effect of a short charge retention half-life can be mitigated to some extent by decreasing the disconnect time ($\tau_1$).

The disconnect time ($\lambda_1$) is an important parameter that can dramatically affect the sensitivity of this measurement. The shorter the disconnect time with respect to the charge retention half-life, the more charge is retained and the better the S/N of the measurement. The limit to how short the disconnect time can be is determined by how rapidly the charging current decays during disconnect. Under the conditions employed in this work, the charging current (for the electrode discharging from $E_{w1}$ to $E_R$, the OCP) decayed exponentially, with a half-life of 0.58 s. In order to make sure that at least 99% of this current has dissipated, one would have to wait at least three $t_{1/2}$, or 1.8 s, prior to reconnection. This discharge time is dependent on the electrical characteristics of the electrochemical cell and potentiostat.

This experiment has been used to evaluate the charge storage capabilities of redox SAMs designed for digital information storage. A wide variety of ZnP-based thiol-tethered molecules have been synthesized and used for charge retention for molecular memory storage (see, e.g., WO 01/03126). The ZnP monolayers have unique charge storage capabilities. The oxidation state of the molecule also affects the charge retention half-life. The half-life of the singly-oxidized ZnP SAM used in this work is 167 s, while that of the doubly-oxidized species is 254 s (Table 1), indicating that the doubly-charged state discharges less rapidly than the singly-charged state. This can be confirmed by comparing the magnitude of stored charge in the two waves. The first wave in this experiment is 21 pC, representing a total of $1.2 \times 10^8$ molecules that hold charge for 15 s. One might expect the magnitude of the limiting charge measured at the second wave to be exactly twice that observed for the first wave, since all the porphyrin molecules that were in the first oxidation state are now doubly oxidized. Instead, the limiting current observed for the second OCP voltammetric wave is almost two and one-half times larger than that found for the singly-oxidized monolayer. This data indicates that the doubly-charged state discharges less rapidly than the singly-charged state, presumably because it is a strongly coupled system, where the second state can only relax via the first state. Investigation of this phenomena may lead to new strategies that prolong the open circuit charge retention behavior of molecules used for tags of biomolecules or for long term memory storage.

OCP Voltammetry of Redox SAMs

Figure 9:
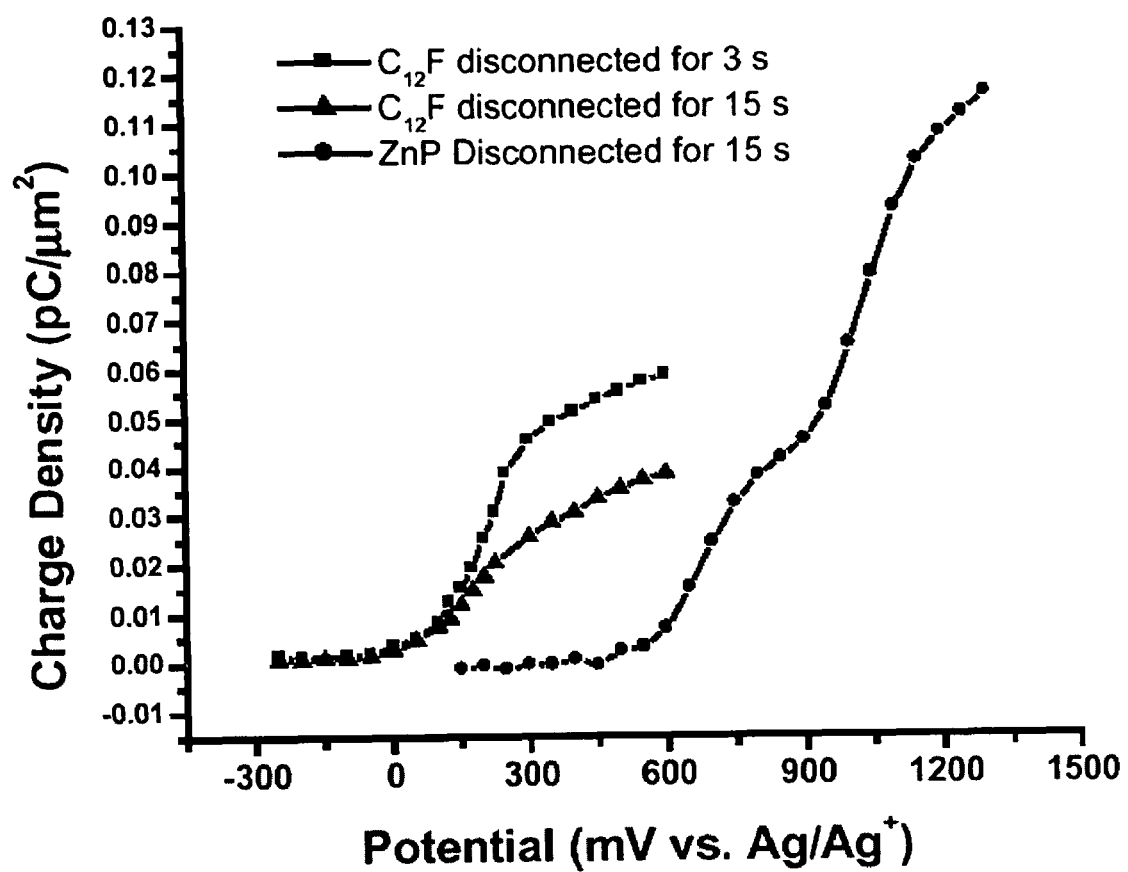
FIG. 9 illustrates open circuit potential voltammetry of the $C_{12}F$ and ZnP SAMs. Each point represents the reductive charge measured after application of a 20 ms oxidizing potential, disconnection ($\tau_1$ as indicated), and reconnection at the OCP (see FIG. 4B). The solid line in each case represents a fit of the sigmoidal current-voltage curve $E=E_{1/2}-(RT/nF)Ln(i_L-i)/i)$, to the observed data. For C12Fc SAM; the oxidizing potential (EW) was varied from −300 mV to 300 mV vs Ag/Ag$^+$ ($\Delta E$=25 mV, $E_R$=−400 mV vs Ag/Ag$^+$). For ZnP SAM; the oxidizing potential was varied from 100 mV to 1250 mV vs Ag/Ag$^+$ ($\Delta E$=50 mV, ER=+125 mV vs Ag/Ag$^+$). The ZnP SAM exhibits two oxidative waves at $E_{1/2}(1)$=0.73 V and E½(s)=1.05 V.

Retention of charge in the oxidized monolayer affords the possibility of collecting voltammetric data as well, simply by performing a series of OCPA steps (similar to pulse voltammetric methods). OCPV is schematically illustrated in FIG. 5B. The top panel in the figure illustrates the pulse sequence for the application of potential to the system; the bottom panel shows the current response. OCPV is implemented by using a series of OCPA steps, where the oxidation potential ($E_{W1}$) is incremented with each step, similar to other pulse voltammetric methods. Unlike those methods, the current is always measured on the reductive step at the OCP ($E_R$). The disconnect time ($\tau_i$) is kept constant while each successive oxidation step is incremented by the same potential step ($\Delta E = E_{w2} - E_{w1}$). As shown in FIG. 9, this allows the creation of a voltammogram, where the reductive current is proportional to the amount of oxidized monolayer that remains after the disconnect time. This follows the Nernst relationship for an equilibrium process, where $E = E_{1/2} + RT/nF \ln(\Gamma_M^+/\Gamma_M^\circ)$, where $\Gamma_M^+$ and $\Gamma_M^\circ$ are the surface concentrations of the oxidized and reduced forms of the monolayer, respectively. This gives rise to a sigmoidal current-voltage relationship, $E = E_{1/2} + RT/nF \ln(i_L - i)/i_L$, where i is the current at any step and $i_L$ is the limiting current at high overpotential. The S/N of the measurement can be improved significantly by integrating the current observed at each step, and plotting the resulting integrated charge (Q). FIG. 9 shows the OCP voltammetry of a $C_{12}F$ SAM, which has a characteristic sigmoidal shape of a Nernstian process. The integrated charge at two discharge times are plotted ($\tau_1 = 3$ s or 15 s, as shown), demonstrating that the sensitivity of the measurement (proportional to $i_L$) is dependent on $\tau_1$, but that the $E_{1/2}$ is independent of discharge time.

The OCP voltammogram for the ZnP SAM is also shown in FIG. 9; it also has virtually no background current (due to the absence of charging current), as shown in the potential range from 150-450 mV. Once the oxidizing step potential starts to approach 650 mV vs Ag/Ag$^+$ (the $E_{1/2}$ for the first oxidation of the ZnP, FIG. 3), the charge read in the reduction at the OCP increases due the greater presence of the singly-oxidized ZnP$^+$. The second oxidation wave is also sigmoidal, and both waves have half-wave potentials which correspond to the $E_{1/2}$ potentials of the ZnP monolayer determined with cyclic voltammetry (650 mV and 1050 mV, respectively; as shown in FIG. 4).

CONCLUSIONS

OCPA can be used to quantitatively determine the amount of stored charge on the surface of an electrode in the absence of charging current. This allows the observation of the unique charge storage capabilities of different SAM forming molecules. The difference in the retention of stored charge between the two types of SAMs is a probably a result of the difference in the cation radical stability in the SAM. OCPV can provide voltammetric information about the redox species involved in the reaction and may be useful in providing qualitative as well as quantitative information about a redox species electrically coupled to an electrode surface.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A molecular memory device comprising:
    a first electrode and a second electrode disposed to contact a redox-active compound comprising a porphyrinic macrocycle and thereby form an electrochemical storage cell wherein said first and second electrodes are fixed electrodes;
    a voltage source connected to said first electrode;
    a switch that allows said compound to be isolated from said voltage source and said storage cell to reach an open circuit potential; and
    a current transducer for measuring current produced by said electrochemical cell; and
    dedicated read/refresh/rewrite circuitry that configured to determine the oxidation state of said compound by:
        activating said switch to isolate said compound from said voltage source thereby allowing said electrochemical cell to reach an open circuit potential (OCP);

then connecting said electrochemical cell to an externally applied potential equivalent to said open circuit potential; and operating said current transducer to detect a resulting current if said current exists wherein the magnitude of said current is a measure of the oxidation state of said compound.

2. The device of claim 1, wherein said device comprises two or more electrochemical cells.

3. The device of claim 2, wherein said device comprises ten or more electrochemical cells.

4. The device of claim 1, wherein said voltage source comprises a voltage follower.

5. The device of claim 1, wherein said current meter comprises a broadband current amplifier.

6. The device of claim 1, wherein said porphyrinic macrocycle is a porphyrin.

7. A molecular memory device comprising: a first electrode and a second electrode disposed to contact a redox-active compound and thereby form an electrochemical storage cell wherein said first and second electrodes are fixed electrodes; a write circuit connected to said first electrode; a switch that allows said compound to be isolated from said write circuit and said storage cell to reach an open circuit potential; a sensing circuit sensitive to current produced by said electrochemical cell; and dedicated read/refresh/rewrite circuitry that determines the oxidation state of said compound by:

activating said switch to isolate said compound from said voltage source thereby allowing said electrochemical cell to reach an open circuit potential (OCP);

then connecting said electrochemical cell to an externally applied potential equivalent to said open circuit potential; and operating said current transducer to detect a resulting current if said current exists wherein the magnitude of said current is a measure of the oxidation state of said compound.

8. The molecular memory of claim 7, wherein said redox-active compound comprises a phorphyrinic macrocycle.

* * * * *

UNITED STATES PATENT AND TRADEMARK OFFICE
CERTIFICATE OF CORRECTION

| | | |
|---|---|---|
| PATENT NO. | : 7,826,250 B2 | |
| APPLICATION NO. | : 11/102089 | |
| DATED | : November 2, 2010 | |
| INVENTOR(S) | : Werner Kuhr et al. | |

It is certified that error appears in the above-identified patent and that said Letters Patent is hereby corrected as shown below:

Title Pg, Item (73), "Assignee:", after "North Carolina State University, Raleigh, NC (US)", add --; The Regents of the University of California, Oakland, CA (US)--.

Signed and Sealed this
Twenty-third Day of August, 2011

David J. Kappos
*Director of the United States Patent and Trademark Office*